(12) United States Patent
Mickiewicz et al.

(10) Patent No.: US 12,053,213 B2
(45) Date of Patent: Aug. 6, 2024

(54) MODULAR SURGICAL INSTRUMENTS AND RELATED METHODS

(71) Applicant: Medos International Sarl, Le Locle (CH)

(72) Inventors: Christopher Mickiewicz, Bridgewater, MA (US); Mark Gracia, Rochester, MA (US); Thomas Runco, Providence, RI (US); Sarah Batchelor, Providence, RI (US); Richard Fournier, New Bedford, MA (US)

(73) Assignee: Medos International Sárl, Le Locle (CH)

( * ) Notice: Subject to any disclaimer, the term of this patent is extended or adjusted under 35 U.S.C. 154(b) by 0 days.

(21) Appl. No.: 17/884,531

(22) Filed: Aug. 9, 2022

(65) Prior Publication Data
US 2023/0085069 A1  Mar. 16, 2023

Related U.S. Application Data

(63) Continuation of application No. 16/815,945, filed on Mar. 11, 2020, now Pat. No. 11,439,441, which is a
(Continued)

(51) Int. Cl.
*A61B 17/70* (2006.01)
*A61B 17/86* (2006.01)
(Continued)

(52) U.S. Cl.
CPC ...... *A61B 17/7082* (2013.01); *A61B 17/7001* (2013.01); *A61B 17/708* (2013.01);
(Continued)

(58) Field of Classification Search
CPC ............ A61B 17/7082; A61B 17/7083; A61B 17/7086; A61B 17/7085; A61B 17/7091
See application file for complete search history.

(56) References Cited

U.S. PATENT DOCUMENTS

| 5,443,467 A | 8/1995 | Biedermann et al. |
| 6,736,820 B2 | 5/2004 | Biedermann et al. |

(Continued)

FOREIGN PATENT DOCUMENTS

| CN | 101052357 A | 10/2007 |
| CN | 1913836 B | 11/2010 |

(Continued)

OTHER PUBLICATIONS

[No Author Listed] Expedium Spine System Surgical Technique Guide, DePuy Spine Inc., 2011, 36 pages.
(Continued)

*Primary Examiner* — Julianna N Harvey
(74) *Attorney, Agent, or Firm* — Barnes & Thornburg LLP

(57) ABSTRACT

Modular surgical instruments and related methods are disclosed herein, e.g., for performing rod reduction, derotation, and/or set screw insertion during spinal surgery. An exemplary system can include an instrument body configured to couple to a bone anchor assembly to provide a modular platform for carrying out various steps of a surgical procedure. For example, the instrument body can receive a reduction instrument therethrough for reducing a spinal rod into the bone anchor assembly. A derotation instrument can be attached to the reduction instrument for performing derotation maneuvers or applying other manipulation forces. A modular driver or handle adapter can be attached to the reduction instrument and/or to the derotation instrument to facilitate rod reduction. Any of the instrument body, the reduction instrument, and the derotation instrument can include a working channel therethrough. A set screw or closure mechanism, and a driver instrument for applying the set screw or closure mechanism to the bone anchor assembly, can be inserted through the working channel.

20 Claims, 23 Drawing Sheets

Related U.S. Application Data continuation of application No. 15/695,335, filed on Sep. 5, 2017, now Pat. No. 10,610,269.

(51) Int. Cl.
  *A61B 17/00* (2006.01)
  *A61B 90/00* (2016.01)

(52) U.S. Cl.
  CPC ........ *A61B 17/7086* (2013.01); *A61B 17/861* (2013.01); *A61B 2017/0046* (2013.01); *A61B 17/7032* (2013.01); *A61B 17/7085* (2013.01); *A61B 17/7091* (2013.01); *A61B 2090/037* (2016.02)

(56) References Cited

U.S. PATENT DOCUMENTS

| | | |
|---|---|---|
| 6,974,460 B2 | 12/2005 | Carbone et al. |
| 7,179,261 B2 | 2/2007 | Sicvol et al. |
| 7,618,444 B2 | 11/2009 | Shluzas |
| 7,918,858 B2 | 4/2011 | Stad et al. |
| 8,137,356 B2 | 3/2012 | Hestad et al. |
| 8,206,395 B2 | 6/2012 | McLean et al. |
| 8,246,623 B2 | 8/2012 | Peultier et al. |
| 8,273,089 B2 | 9/2012 | Jackson |
| 8,303,595 B2 | 11/2012 | Jones |
| 8,308,774 B2 | 11/2012 | Hoffman et al. |
| 8,439,924 B1 | 5/2013 | McBride et al. |
| 8,460,308 B2 | 6/2013 | Marino et al. |
| 8,540,718 B2 | 9/2013 | Dauster et al. |
| 8,556,903 B2 | 10/2013 | Miller et al. |
| 8,556,904 B2 | 10/2013 | Rezach et al. |
| 8,845,649 B2 | 9/2014 | Jackson |
| 8,906,062 B2 | 12/2014 | Nichols et al. |
| 8,986,349 B1 | 3/2015 | German et al. |
| 9,060,817 B2 | 6/2015 | Justis |
| 9,066,761 B2 | 6/2015 | McBride et al. |
| 9,078,709 B2 | 7/2015 | McBride |
| 9,149,307 B2 | 10/2015 | Sandstrom et al. |
| 9,186,188 B2 | 11/2015 | Gleason et al. |
| 9,204,909 B2 | 12/2015 | Rezach et al. |
| 9,220,539 B2 | 12/2015 | McBride et al. |
| 9,220,543 B2 | 12/2015 | Walker et al. |
| 9,241,743 B2 | 1/2016 | Hopkins et al. |
| 9,247,969 B2 | 2/2016 | Nunley et al. |
| 9,265,533 B2 | 2/2016 | Nelson et al. |
| 9,468,474 B2 | 10/2016 | Parikh et al. |
| 9,517,099 B2 | 12/2016 | Bess et al. |
| 9,743,962 B2 | 8/2017 | Viart et al. |
| 9,833,268 B2 | 12/2017 | Walker |
| 9,901,378 B2 | 2/2018 | Dauster et al. |
| 9,918,752 B2 | 3/2018 | Hennard et al. |
| 9,943,343 B2 | 4/2018 | Meyer et al. |
| 9,962,197 B2 | 5/2018 | Dandaniopoulos et al. |
| 10,028,771 B2 | 7/2018 | Artaki et al. |
| 10,039,578 B2 | 8/2018 | Anderson et al. |
| 10,064,662 B2 | 9/2018 | Gunn et al. |
| 10,085,778 B2 | 10/2018 | Semingson et al. |
| 10,154,862 B2 | 12/2018 | Miller et al. |
| 10,166,050 B2 | 1/2019 | Heuer |
| 10,299,839 B2 | 5/2019 | Sicvol et al. |
| 10,398,481 B2 | 9/2019 | Goel et al. |
| 10,433,884 B2 | 10/2019 | Barrett et al. |
| 10,524,843 B2 | 1/2020 | Mladenov et al. |
| 10,568,669 B2 | 2/2020 | Reitblat et al. |
| 10,610,269 B2 | 4/2020 | Mickiewicz et al. |
| 10,675,066 B2 | 6/2020 | George |
| 10,682,167 B2 | 6/2020 | Sandstrom et al. |
| 10,702,315 B2 | 7/2020 | Lindner |
| 10,709,477 B2 | 7/2020 | Manninen et al. |
| 10,716,602 B2 | 7/2020 | Fischer |
| 10,729,477 B2 | 8/2020 | Cain et al. |
| 11,439,441 B2 | 9/2022 | Mickiewicz et al. |
| 2006/0036255 A1 | 2/2006 | Pond, Jr. et al. |
| 2006/0074418 A1 | 4/2006 | Jackson |
| 2006/0074445 A1 | 4/2006 | Gerber et al. |
| 2007/0093817 A1 | 4/2007 | Barrus et al. |
| 2007/0191841 A1 | 8/2007 | Justis et al. |
| 2007/0213714 A1 | 9/2007 | Justis |
| 2008/0015601 A1 | 1/2008 | Castro et al. |
| 2008/0077138 A1 | 3/2008 | Cohen et al. |
| 2008/0228233 A1 | 9/2008 | Hoffman et al. |
| 2009/0228055 A1 | 9/2009 | Jackson |
| 2010/0114174 A1 | 5/2010 | Jones et al. |
| 2010/0121385 A1 | 5/2010 | Blain et al. |
| 2011/0077690 A1 | 3/2011 | Shin et al. |
| 2011/0263945 A1* | 10/2011 | Peterson ............ A61B 17/7086 606/300 |
| 2011/0288599 A1 | 11/2011 | Michielli et al. |
| 2012/0191144 A1 | 7/2012 | Peultier et al. |
| 2013/0018419 A1 | 1/2013 | Rezach et al. |
| 2013/0053901 A1 | 2/2013 | Cormier et al. |
| 2013/0096618 A1 | 4/2013 | Chandanson et al. |
| 2013/0103039 A1 | 4/2013 | Hopkins et al. |
| 2013/0103094 A1 | 4/2013 | Beale et al. |
| 2013/0238030 A1 | 9/2013 | Steib |
| 2013/0317558 A1 | 11/2013 | Varieur et al. |
| 2014/0052197 A1 | 2/2014 | McBride et al. |
| 2014/0074106 A1 | 3/2014 | Shin |
| 2014/0142585 A1 | 5/2014 | Rutledge |
| 2014/0148865 A1* | 5/2014 | Hennard ............ A61B 17/7086 606/86 A |
| 2014/0180298 A1 | 6/2014 | Stevenson et al. |
| 2014/0276894 A1 | 9/2014 | Ramsay et al. |
| 2014/0276896 A1 | 9/2014 | Harper |
| 2014/0277167 A1 | 9/2014 | Hutton et al. |
| 2014/0277170 A1 | 9/2014 | Barrett et al. |
| 2014/0277206 A1 | 9/2014 | Reitblat et al. |
| 2014/0311264 A1 | 10/2014 | Black et al. |
| 2014/0316475 A1 | 10/2014 | Parikh et al. |
| 2015/0039035 A1 | 2/2015 | Krüger |
| 2015/0066042 A1 | 3/2015 | Cummins et al. |
| 2015/0066089 A1 | 3/2015 | Nelson et al. |
| 2015/0112397 A1 | 4/2015 | Petit |
| 2015/0148849 A1 | 5/2015 | Abidin |
| 2015/0173807 A1 | 6/2015 | Artaki et al. |
| 2015/0351810 A1 | 12/2015 | Lindner et al. |
| 2016/0022317 A1 | 1/2016 | Kraus |
| 2016/0030093 A1 | 2/2016 | Walker |
| 2016/0089188 A1 | 3/2016 | McBride, Jr. et al. |
| 2016/0235450 A1 | 8/2016 | Walker et al. |
| 2016/0367296 A1 | 12/2016 | Walker |
| 2017/0100116 A1 | 4/2017 | Erramilli et al. |
| 2017/0143385 A1 | 5/2017 | Biyani et al. |
| 2017/0164980 A1 | 6/2017 | Le Roux et al. |
| 2018/0055545 A1 | 3/2018 | Biedermann et al. |
| 2018/0116703 A1 | 5/2018 | Schäfer et al. |
| 2018/0185072 A1 | 7/2018 | Rubin et al. |
| 2019/0069934 A1 | 3/2019 | Mickiewicz et al. |
| 2019/0117280 A1 | 4/2019 | Avidano et al. |
| 2019/0183542 A1 | 6/2019 | Lish et al. |
| 2019/0231400 A1 | 8/2019 | Jackson et al. |
| 2019/0274740 A1 | 9/2019 | Stoll et al. |
| 2019/0380748 A1 | 12/2019 | Doose et al. |
| 2019/0380750 A1 | 12/2019 | Morris |
| 2020/0093521 A1 | 3/2020 | Klausman et al. |
| 2020/0205864 A1 | 7/2020 | Mickiewicz et al. |
| 2020/0367939 A1 | 11/2020 | Loftis et al. |
| 2022/0280207 A1 | 9/2022 | Biester et al. |

FOREIGN PATENT DOCUMENTS

| | | |
|---|---|---|
| DE | 102011103252 A1 | 11/2012 |
| JP | 2008514365 A | 5/2008 |
| JP | 2014176705 A | 9/2014 |
| WO | 2009158707 A1 | 12/2009 |
| WO | 2011133160 A1 | 10/2011 |
| WO | 2015140440 A1 | 9/2015 |
| WO | 2015145343 A1 | 10/2015 |

OTHER PUBLICATIONS

A Solutions for Simple and Complex Spine Pathology MATRIX

(56) References Cited

OTHER PUBLICATIONS

Spine System Degenerative Surgical Technique (2017) DePuySynthes.
Chinese Office Action for Application No. 201880057651.0, dated Feb. 21, 2023 (19 pages).
International Search Report and Written Opinion for Application No. PCT/US18/47130, mailed Nov. 9, 2018 (10 pages).
Extended European Search Report for Application No. 18853556.1, issued May 3, 2021 (7 pages).
Japanese Search Report for Application No. 2020-534162, issued Jun. 6, 2022 (22 pages).
European Examination Report for Application No. 18853556.1 dated Jun. 12, 2024 (6 pages).

* cited by examiner

FIG. 1A
PRIOR ART
FIG. 1B
PRIOR ART
FIG. 1C
PRIOR ART
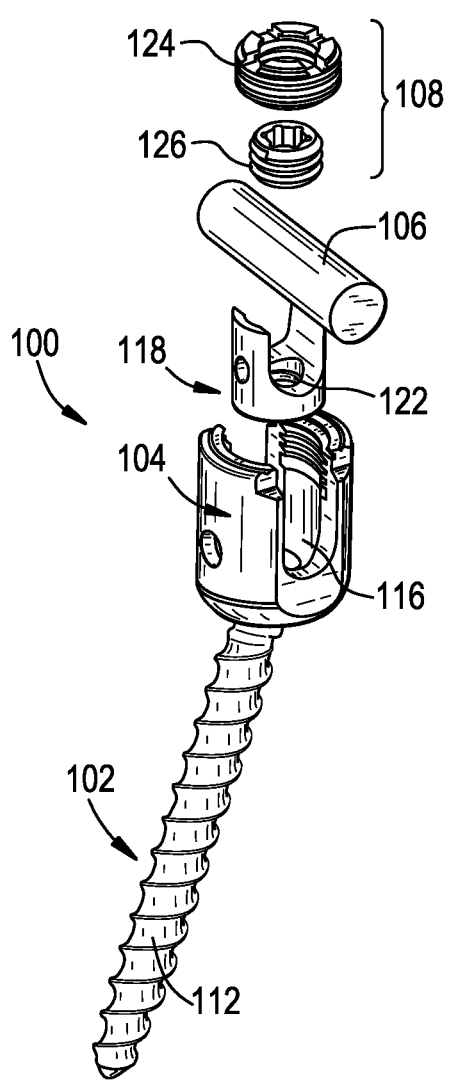
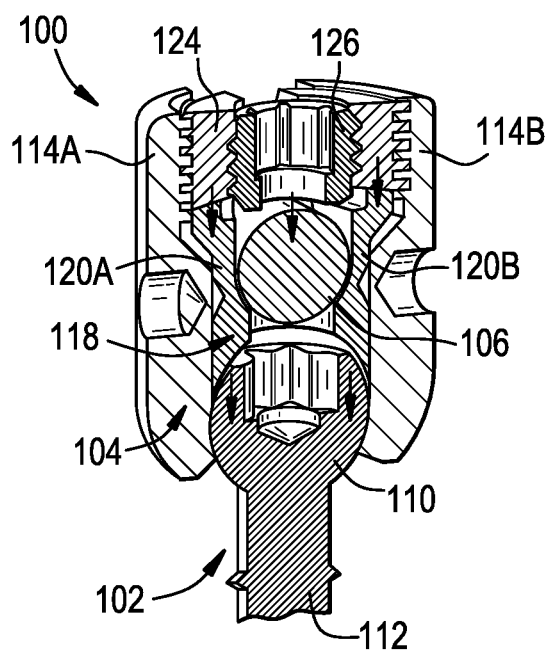
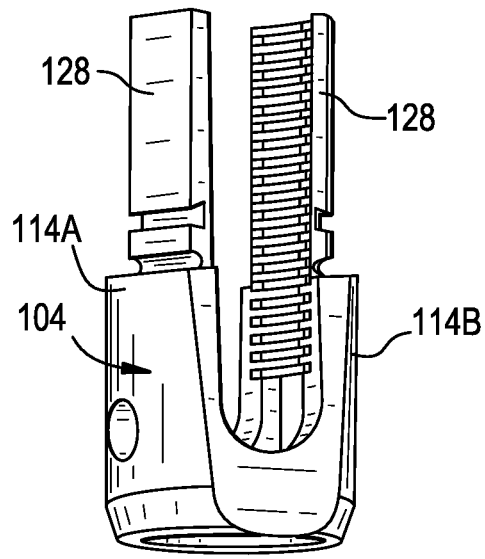

FIG. 10A
FIG. 10B
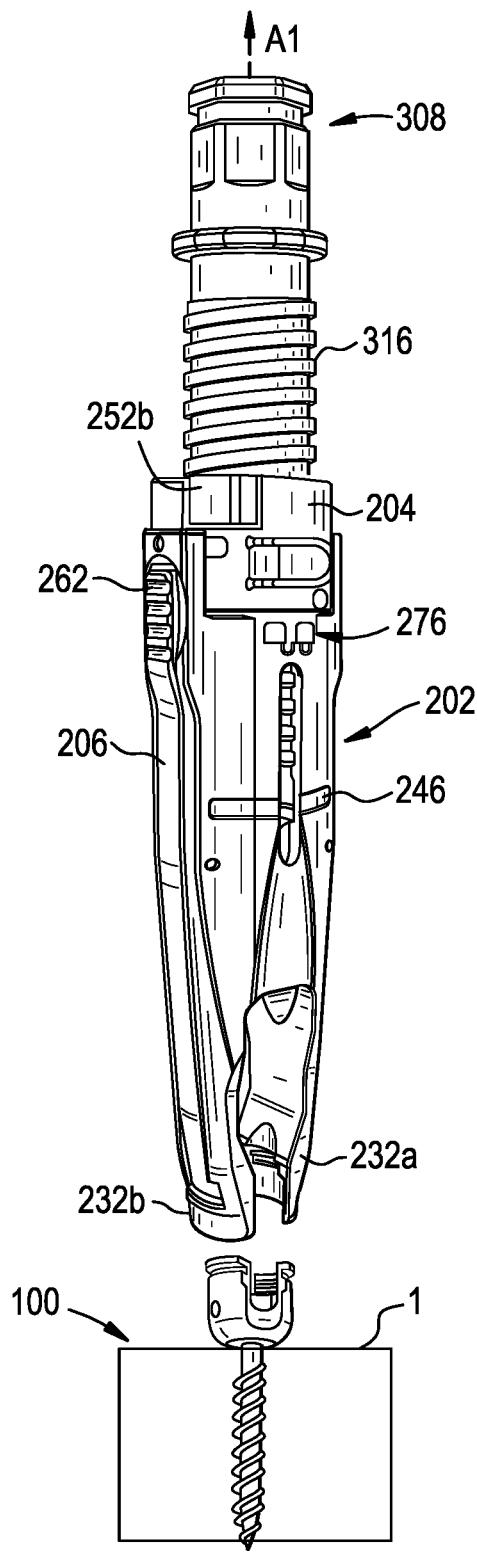
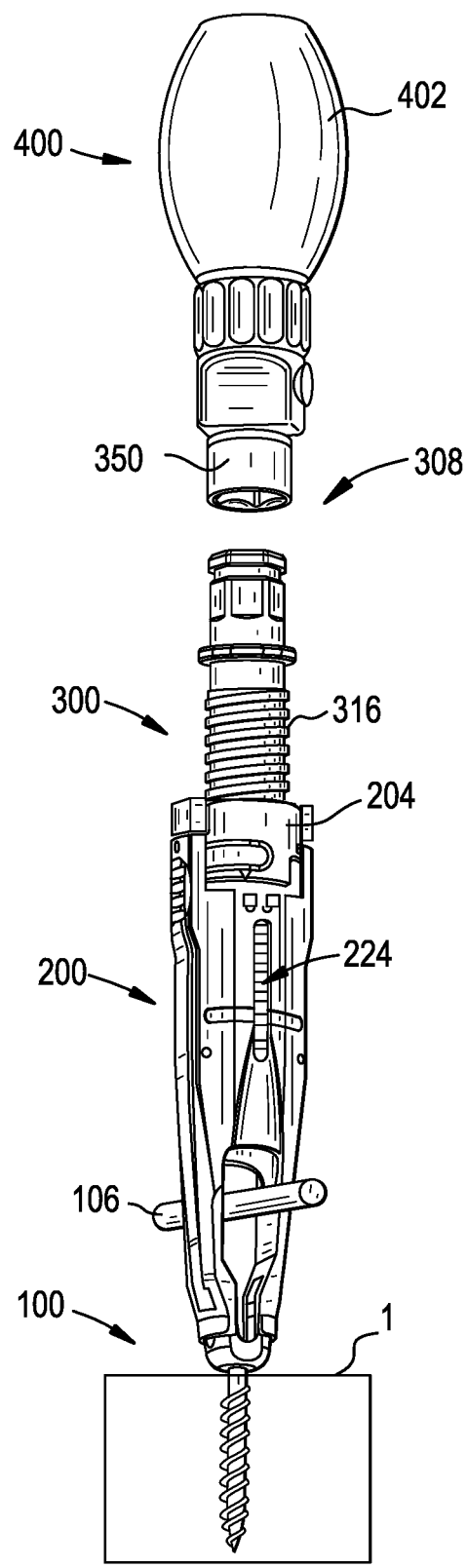

FIG. 10C
FIG. 10D
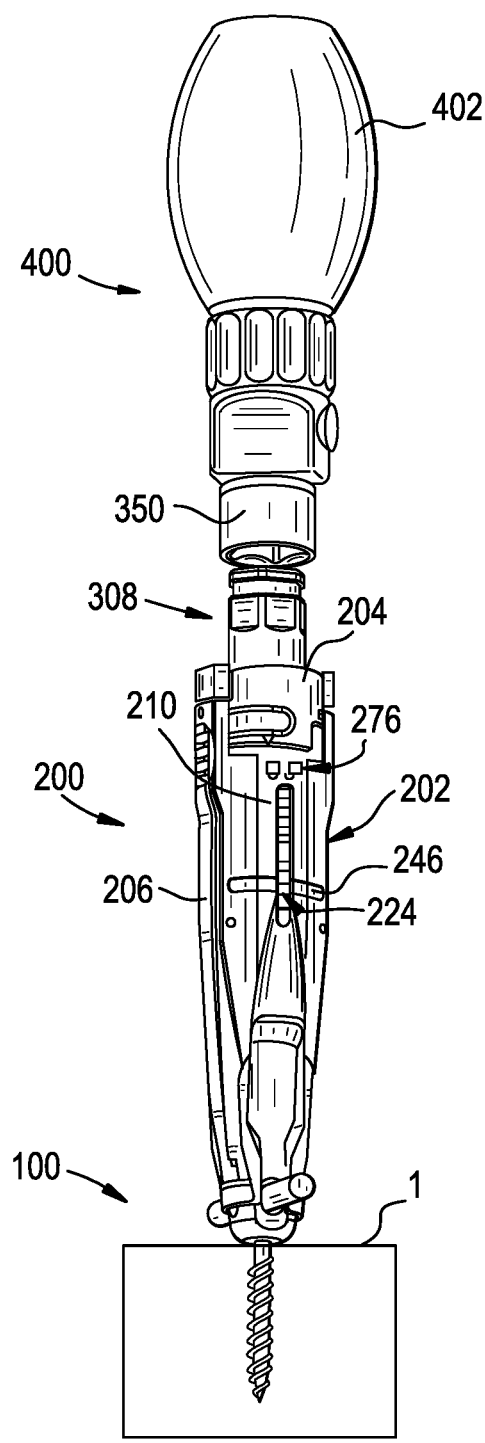
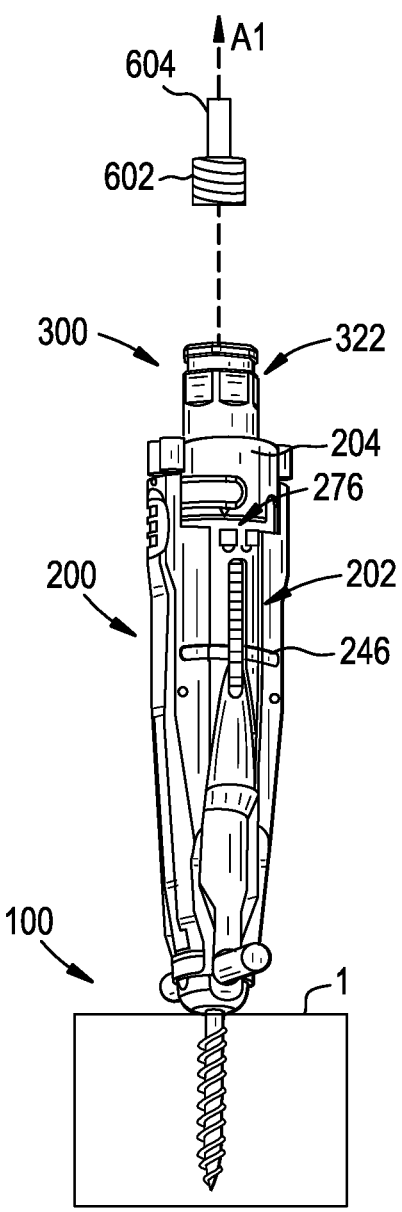

FIG. 10E
FIG. 10F
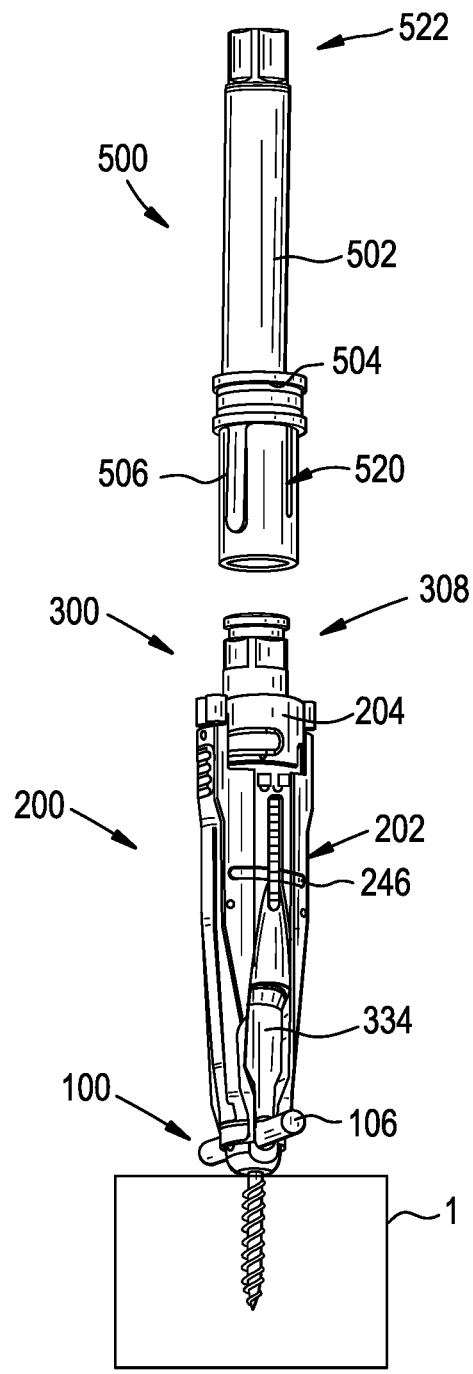
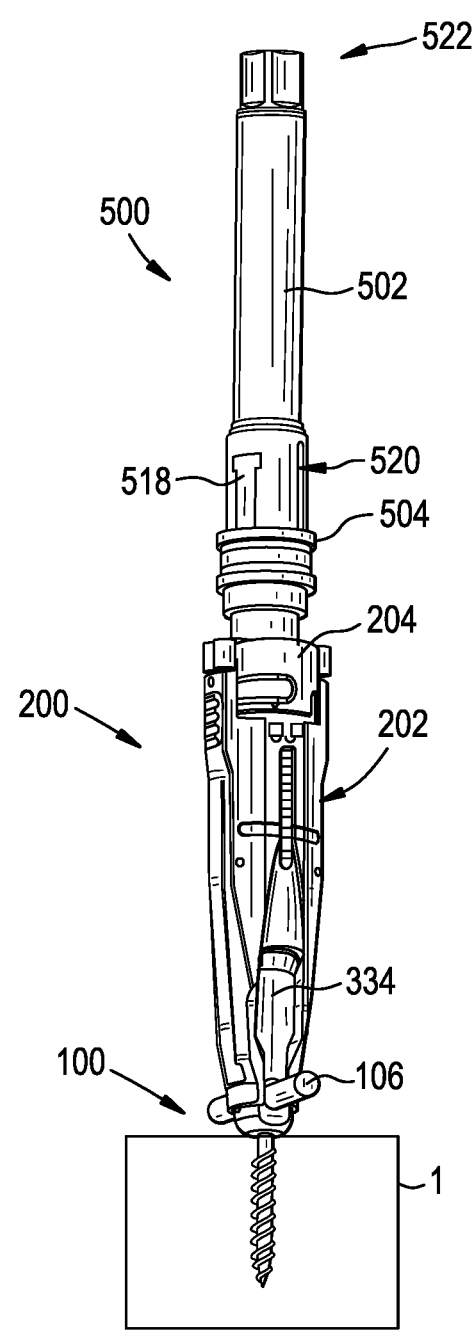

FIG. 10G
FIG. 10H
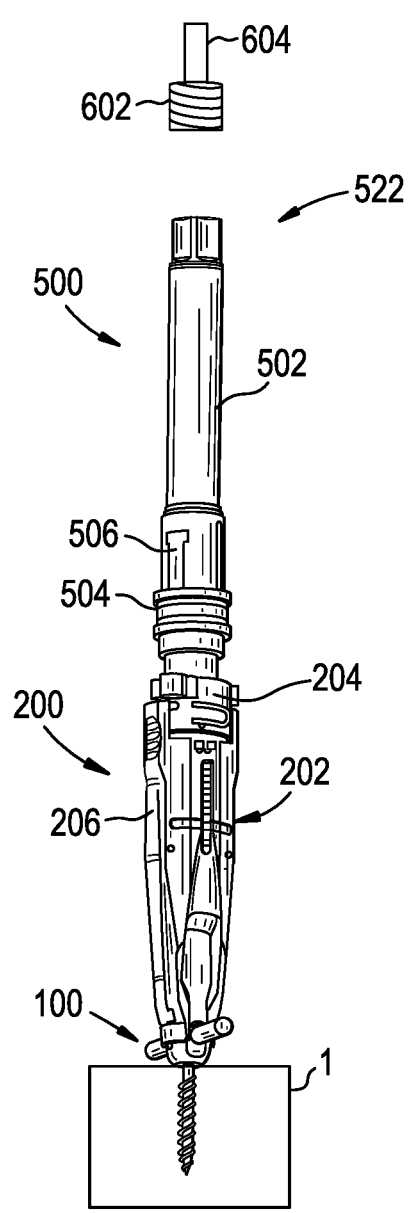
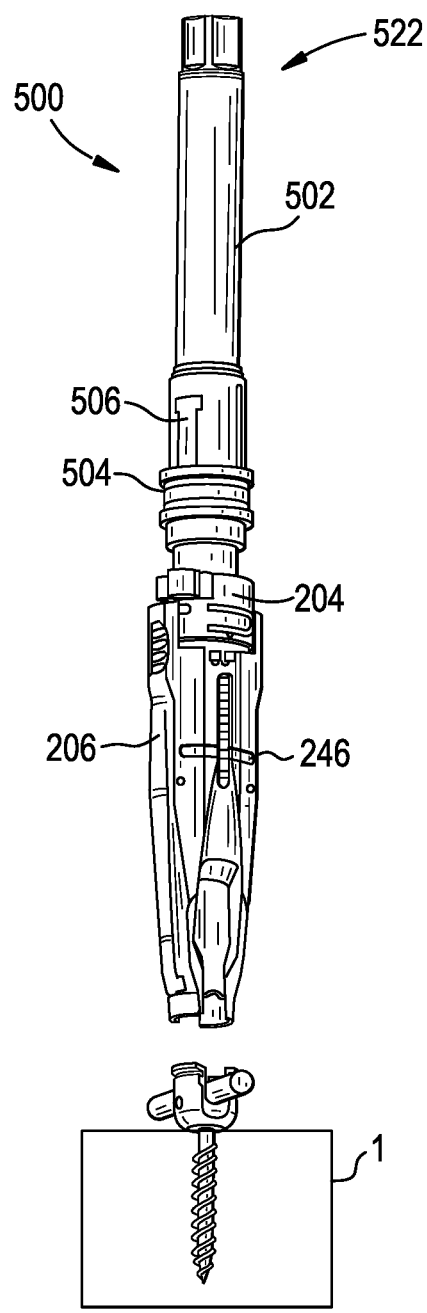

MODULAR SURGICAL INSTRUMENTS AND RELATED METHODS

CROSS-REFERENCE TO RELATED APPLICATIONS

This application is a continuation of U.S. application Ser. No. 16/815,945, filed Mar. 11, 2020. U.S. application Ser. No. 16/815,945 is a continuation of U.S. application Ser. No. 15/695,335, filed Sep. 5, 2017, now issued as U.S. Pat. No. 10,610,269. The entire contents of each of these applications are hereby incorporated by reference.

FIELD

Modular surgical instruments and related methods are disclosed herein, e.g., for performing rod reduction, derotation, and/or set screw insertion during spinal surgery.

BACKGROUND

Fixation systems can be used in orthopedic surgery or neurosurgery to maintain a desired spatial relationship between multiple bones or bone fragments. For example, in spinal surgery, a spinal fixation system can be implanted into a patient to align and/or fix a desired orientation of one or more vertebrae. A typical spinal fixation system can include bone anchors implanted in the vertebrae and longitudinal rods that are secured to the bone anchors by set screws or other closure mechanisms. Implanting the fixation system can involve multiple steps, e.g., rod reduction, derotation, set screw insertion, among others.

Traditionally, multiple separate instruments have been required to perform these steps. Accordingly, a large number of instruments must be prepared and made available during the surgery, the surgeon must repeatedly switch between several different instruments, and frequent insertion, removal, and re-insertion of instruments to and from the surgical site can be required. All of this can lead to surgeon fatigue, prolonged operating time, and patient risks associate therewith.

SUMMARY

Modular surgical instruments and related methods are disclosed herein, e.g., for performing rod reduction, derotation, and/or set screw insertion during spinal surgery. An exemplary system can include an instrument body configured to couple to a bone anchor assembly to provide a modular platform for carrying out various steps of a surgical procedure. For example, the instrument body can receive a reduction instrument therethrough for reducing a spinal rod into the bone anchor assembly. A derotation instrument can be attached to the reduction instrument for performing derotation maneuvers or applying other manipulation forces. A modular driver or handle adapter can be attached to the reduction instrument and/or to the derotation instrument to facilitate rod reduction. Any of the instrument body, the reduction instrument, and the derotation instrument can include a working channel therethrough. A set screw or closure mechanism, and a driver instrument for applying the set screw or closure mechanism to the bone anchor assembly, can be inserted through the working channel.

In some embodiments, a surgical instrument can include a housing having a central opening, a proximal end, a distal end, and a central longitudinal axis A1 extending between the proximal and distal ends; first and second fixed arms extending distally from the housing; first and second pivoting arms movably coupled to the housing, each pivoting arm having a proximal end and a distal end, the pivoting arms being configured to selectively retain a bone anchor therebetween; and a locking member that is movable relative to the housing between a locked position and an unlocked position, wherein: in the locked position, a blocking portion of the locking member is aligned with the pivoting arms and interferes with movement of the pivoting arms relative to the housing; and in the unlocked position, a relief portion of the locking member is aligned with the pivoting arms such that the arms are free to move relative to the housing.

The pivoting arms can be mounted in recesses formed in the fixed arms. The pivoting arms can be pivotally coupled to the housing at a location intermediate the proximal and distal ends of the pivoting arms. The blocking and relief portions of the locking member can be positionable adjacent to and radially-inward from the proximal ends of the pivoting arms. The locking member can include a ring that is rotatable relative to the housing about the axis A1 to move between the locked and unlocked positions. The locking member can include a ring that is translatable relative to the housing along the axis A1 to move between the locked and unlocked positions. The housing can include a tubular central portion with opposed wings extending laterally therefrom, the pivoting arms being mounted in the opposed wings. The locking member can include a biased mating tab that selectively engages recesses formed in a sidewall of the housing to maintain a position of the locking member relative to the housing.

The instrument can include reducer shaft threadably mounted in the central opening of the housing. The reducer shaft can include a first portion having an exterior thread and being configured to rotate relative to the housing to advance the reducer shaft distally relative to the housing. The reducer shaft can include a second portion that is rotationally-fixed relative to the housing, the second portion comprising a distal-facing rod-engaging surface. The first portion can include one or more resilient arms engaged with a circumferential groove formed in an interior surface of the second portion. The reducer shaft can define a working channel extending therethrough. The reducer shaft can include a drive interface at a proximal end of the reducer shaft.

The instrument can include a derotation shaft selectively attachable to the reducer shaft. The derotation shaft can include an elongate body defining a working channel extending therethrough, the working channel of the derotation shaft being in communication with a working channel of the reducer shaft and the central opening of the housing. The derotation shaft can include opposed hinged arms and a locking ring, wherein the locking ring is movable between a locked position in which the locking ring urges the hinged arms radially inward to engage a groove formed in the reducer shaft and an unlocked position in which the hinged arms can move radially outward to disengage from the groove of the reducer shaft. The derotation shaft can include a drive interface at a proximal end of the derotation shaft.

In some embodiments, a surgical method can include implanting a bone anchor in a bone of a patient, the bone anchor comprising a receiver member having a rod seat; positioning an instrument body in an unlocked configuration, the instrument body having a housing, opposed fixed arms extending distally from the housing and defining a rod slot therebetween, opposed pivoting arms movably coupled to the housing, a locking member, and a working channel extending through the instrument body, wherein the pivoting arms are free to pivot relative to the housing when the instrument body is in the unlocked configuration; moving distal ends of the pivoting arms apart from one another; positioning the bone anchor between the fixed arms of the instrument body such that the rod slot of the instrument body is aligned with the rod seat of the bone anchor; moving the distal ends of the pivoting arms towards one another to engage a mating feature of the bone anchor; positioning the instrument body in a locked configuration, wherein the locking member interferes with movement of the pivoting arms relative to the housing when the instrument body is in the locked configuration, thereby preventing the pivoting arms from disengaging from the mating feature of the bone anchor.

The method can include placing a rod within the rod slot and advancing a reducer shaft through the working channel of the instrument body to urge the rod distally into the rod seat of the bone anchor. The method can include attaching a handle or driver adapter to the reducer shaft and applying torque to the handle or driver adapter to rotate the reducer shaft. The method can include inserting a set screw through a working channel of the reducer shaft and through the working channel of the instrument body and securing the set screw to the bone anchor. A step of reducing the rod into the rod seat and a step of securing the set screw to the bone anchor can be performed without disconnecting the instrument body from the bone anchor between said steps.

The method can include attaching a derotation shaft to the reducer shaft and applying a manipulation force to the derotation shaft to reposition the bone of the patient. The method can include inserting a set screw through a working channel of the derotation shaft, through a working channel of the reducer shaft, and through the working channel of the instrument body, and securing the set screw to the bone anchor. A step of applying the manipulation force, a step of reducing the rod into the rod seat, and a step of securing the set screw to the bone anchor can be performed without disconnecting the instrument body from the bone anchor between said steps. Attaching the derotation shaft can include inserting a male drive interface of the reducer shaft into a female drive interface of the derotation shaft. Attaching the derotation shaft can include moving hinged arms of the derotation shaft into engagement with a groove formed in the reducer shaft. The hinged arms can be moved into engagement with the groove by rotating or axially translating a locking ring along an exterior surface of the derotation shaft. The method can include attaching a handle or driver adapter to the derotation shaft and applying torque to the handle or driver adapter to rotate the derotation shaft and the reducer shaft. The bone anchor can be implanted after attaching the instrument body to the bone anchor. The bone anchor can be implanted using a driver shaft inserted through the working channel of the instrument body while the instrument body is attached to the bone anchor.

BRIEF DESCRIPTION OF THE DRAWINGS

The following detailed description is provided with the accompanying drawings, in which:

FIG. 1A is an exploded perspective view of a prior art bone anchor assembly;

FIG. 1B is a sectional view of the bone anchor assembly of FIG. 1A;

FIG. 1C is a perspective view of the bone anchor assembly of FIG. 1A shown with extension tabs;

FIG. 10A is a perspective view of the instruments herein in use during a step of a surgical procedure;

FIG. 10B is a perspective view of the instruments herein in use during another step of the surgical procedure;

FIG. 10C is a perspective view of the instruments herein in use during another step of the surgical procedure;

FIG. 10D is a perspective view of the instruments herein in use during another step of the surgical procedure;

FIG. 10E is a perspective view of the instruments herein in use during another step of the surgical procedure;

FIG. 10F is a perspective view of the instruments herein in use during another step of the surgical procedure;

FIG. 10G is a perspective view of the instruments herein in use during another step of the surgical procedure; and FIG. 10H is a perspective view of the instruments herein in use during another step of the surgical procedure.

DETAILED DESCRIPTION

Figure 2A:
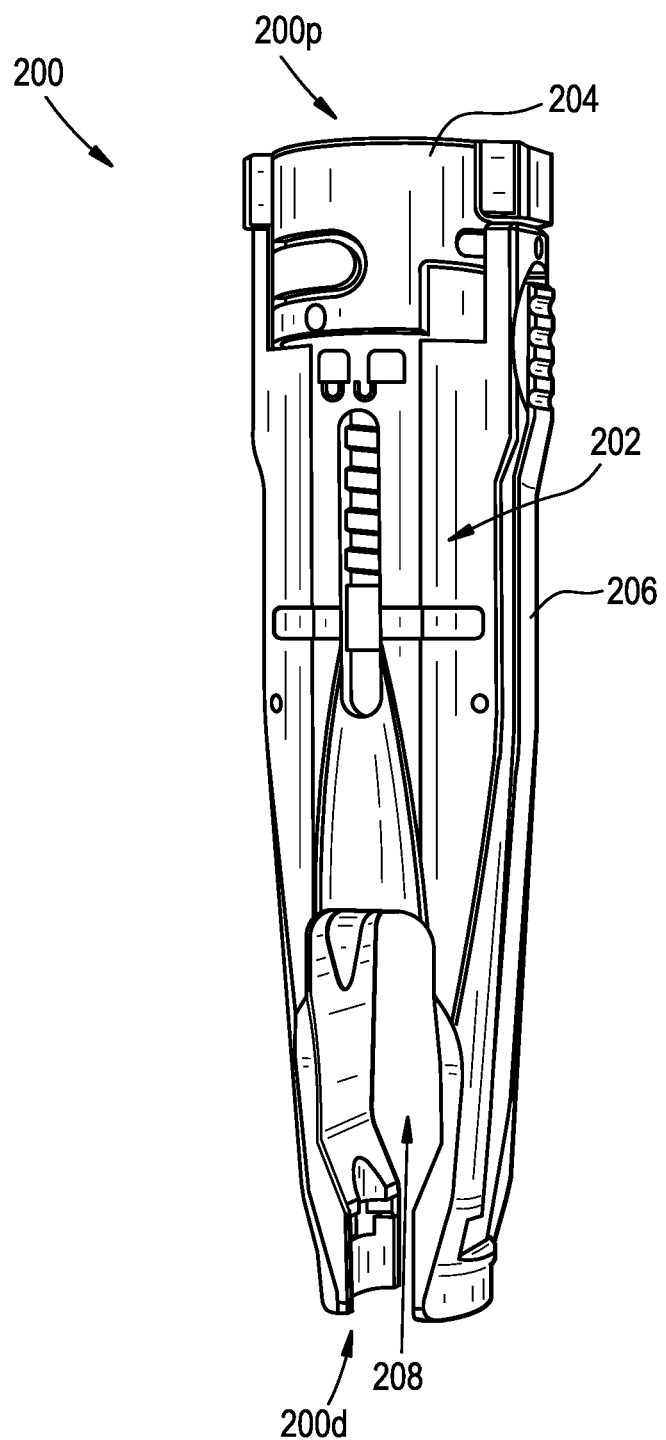
FIG. 2A is a perspective view of an instrument body.

Modular surgical instruments and related methods are disclosed herein, e.g., for performing rod reduction, derotation, and/or set screw insertion during spinal surgery. An exemplary system can include an instrument body configured to couple to a bone anchor assembly to provide a modular platform for carrying out various steps of a surgical procedure. For example, the instrument body can receive a reduction instrument therethrough for reducing a spinal rod into the bone anchor assembly. A derotation instrument can be attached to the reduction instrument for performing derotation maneuvers or applying other manipulation forces. A modular driver or handle adapter can be attached to the reduction instrument and/or to the derotation instrument to facilitate rod reduction. Any of the instrument body, the reduction instrument, and the derotation instrument can include a working channel therethrough. A set screw or closure mechanism, and a driver instrument for applying the set screw or closure mechanism to the bone anchor assembly, can be inserted through the working channel.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Bone Anchor Assembly

FIGS. 1A-1C illustrate a prior art bone anchor assembly 100 with which the surgical instruments disclosed herein can be used. It will be appreciated that the illustrated bone anchor assembly 100 is exemplary and that other bone anchor assemblies having additional or alternative features can be used with the instruments herein.

The illustrated bone anchor assembly 100 includes a bone anchor or shank 102, a receiver member 104 for receiving a spinal fixation element, such as a spinal rod 106, to be coupled to the bone anchor 102, and a closure mechanism 108 to capture a spinal fixation element within the receiver member and fix the spinal fixation element with respect to the receiver member. The bone anchor 102 includes a proximal head 110 and a distal shaft 112 configured to engage bone. The receiver member 104 has a proximal end having a pair of spaced apart arms 114A, 114B defining a recess 116 therebetween and a distal end having a distal end surface defining an opening through which at least a portion of the bone anchor 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the bone anchor 102 is generally in the shape of a truncated sphere having a planar proximal surface and an approximately spherically-shaped distal surface. The illustrated bone anchor assembly 100 is a polyaxial bone screw designed for posterior implantation in the pedicle or lateral mass of a vertebra. The proximal head 110 of the bone anchor 102 engages the distal end of the receiver member 104 in a ball and socket like arrangement in which the proximal head and the distal shaft 112 can pivot relative to the receiver member. The distal surface of the proximal head 110 of the bone anchor 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the bone anchor 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the bone anchor 102 can be cannulated, having a central passage or cannula extending the length of the bone anchor to facilitate delivery of the bone anchor over a guidewire in, for example, minimally-invasive procedures. Other components of the bone anchor assembly 100, including, for example, the closure mechanism 108, the receiver member 104, and the compression member or cap 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the bone anchor 102. The sidewall openings can extend radially from the cannula through the sidewall of the distal shaft 112. Exemplary systems for delivering bone cement to the bone anchor assembly 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the bone anchor 102 can also be coated with materials to permit bone growth, such as, for example, hydroxyapatite, and the bone anchor assembly 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments, e.g., instruments of the type described herein. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the bone anchor 102 extends. For example, the distal shaft 112 of the bone anchor 102 can extend through the opening.

The bone anchor 102 can be selectively fixed relative to the receiver member 104. Prior to fixation, the bone anchor 102 is movable relative to the receiver member 104 within a cone of angulation generally defined by the geometry of the distal end of the receiver member and the proximal head 110 of the bone anchor 102. The bone anchor assembly 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly 100 can be a conventional (non-biased) polyaxial screw in which the bone anchor 102 pivots in the same amount in every direction.

The spinal fixation element, e.g., the spinal rod 106, can either directly contact the proximal head 110 of the bone anchor 102 or can contact an intermediate element, e.g., a compression member 118. The compression member 118 can be positioned within the receiver member 104 and interposed between the spinal rod 106 and the proximal head 110 of the bone anchor 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the bone anchor 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the bone anchor 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. The receiver member 104 can include, can be formed integrally with, or can be coupled to one or more extension tabs 128 (shown in FIG. 1C) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor assembly 100 can be used with a spinal fixation element such as rigid spinal rod 106. Alternatively, the spinal fixation element can be a dynamic stabilization member that allows controlled mobility between the instrumented vertebrae.

In use, the bone anchor assembly 100 can be assembled such that the distal shaft 112 extends through the opening in the distal end of the receiver member 104 and the proximal head 110 of the bone anchor 102 is received in the distal end of the receiver member 104. A driver instrument can be fitted with the bone anchor 102 to drive the bone anchor into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the bone anchor 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the bone anchor 102, thereby locking the angular position of the bone anchor 102 relative to the receiver member 104. A torsional force can be applied to the inner set screw 126 to force the spinal rod 106 into engagement with the compression member 118 and thereby fix the spinal rod 106 relative to the receiver member 104.

The instruments disclosed herein can be configured to operate in conjunction with bone anchor assemblies of the type described above or other types known in the art. Exemplary bone anchor assemblies include monoaxial screws, polyaxial screws, uniplanar screws, favored-angle screws, and/or any of a variety of other bone anchor types known in the art. Further information on favored-angle screws can be found in U.S. Patent Application Publication No. 2013/0096618, filed on Oct. 9, 2012, which is hereby incorporated by reference herein. Bone anchor assemblies are sometimes referred to herein simply as "bone anchors."

Modular Surgical Instruments and Related Methods

Figure 2B:
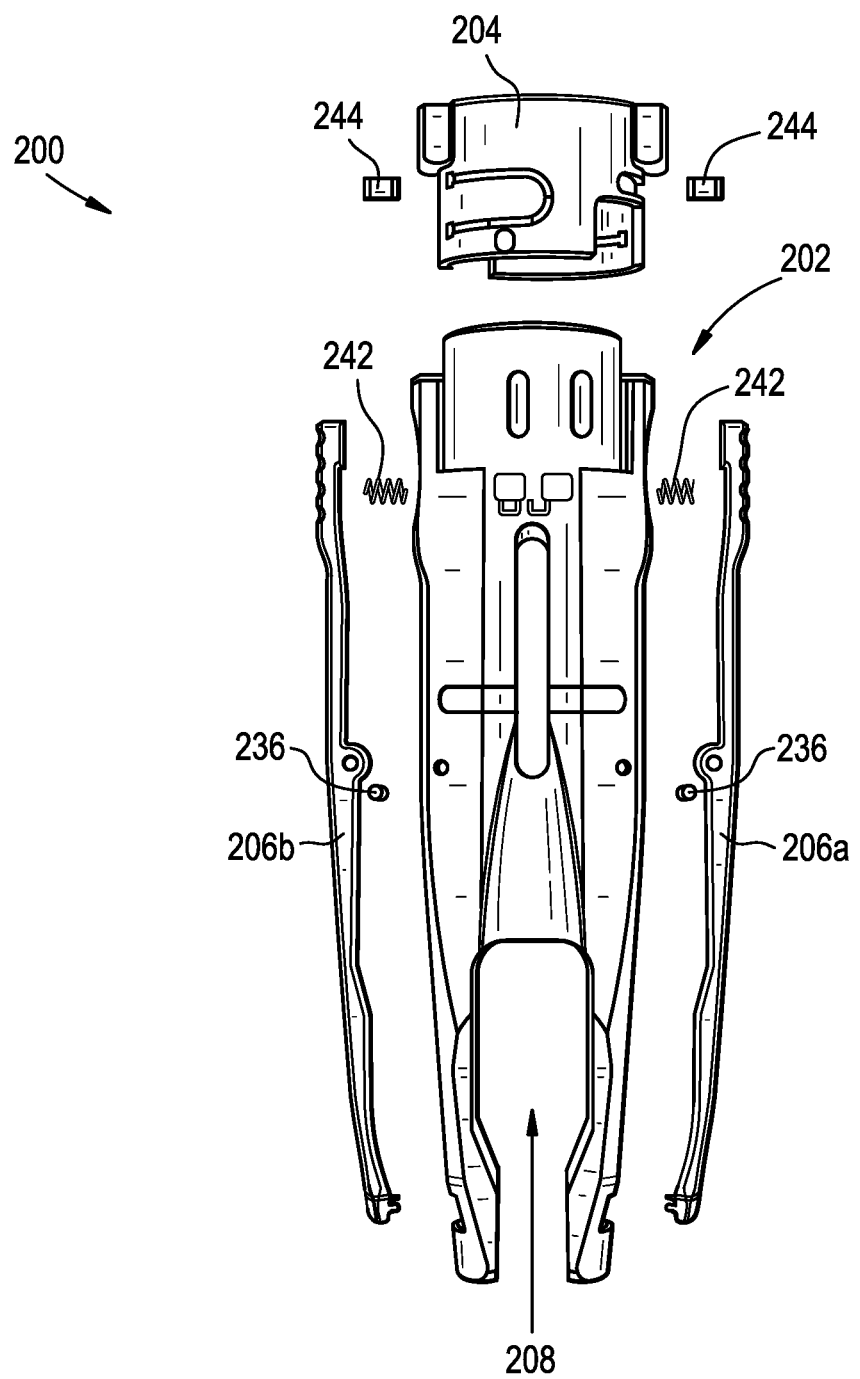
FIG. 2B is an exploded perspective view of the instrument body of FIG. 2A.
Figure 2C:
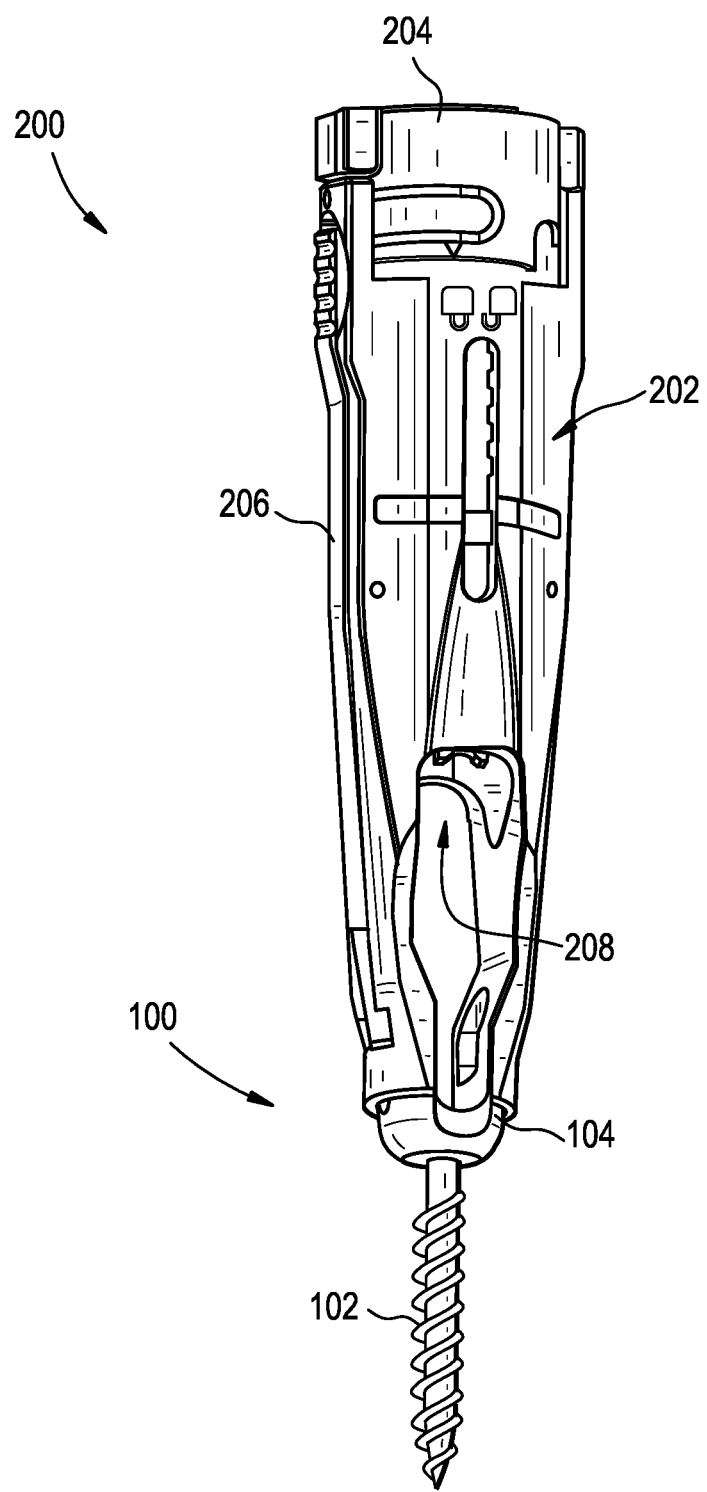
FIG. 2C is a perspective view of the instrument body of FIG. 2A docked to a bone anchor assembly.

FIGS. 2A-2C illustrate an exemplary instrument body 200 that can be used to provide a platform for various surgical steps, such as rod reduction, derotation, and/or set screw insertion. The instrument body 200 can include a housing 202, a locking member 204 rotatably and/or slidably disposed on the housing 202, and a pair of pivoting arms 206 attached to the housing 202. The instrument body 200 can define a working channel 208 configured to receive at least a portion of another tool or instrument, e.g., a reduction instrument or reducer shaft 300, therein. The channel 208 can provide access to the surgical site to allow passage of instruments or implants therethrough. The channel 208 can extend from a proximal end 200p of the instrument body 200 to a distal end 200d of the instrument body.

In use, the instrument body 200 can be positioned such that the pivoting arms 206a, 206b engage a bone anchor 100 disposed therebetween to dock the instrument body 200 to the bone anchor 100, e.g., as shown in FIG. 2C. The locking member 204 can be movable between an unlocked position and a locked position to lock the instrument body 200 to the bone anchor 100. For example, the locking member 204 can be rotated or axially translated relative to the instrument body 200 to selectively prevent the arms 206a, 206b from pivoting, thereby locking the instrument body to the bone anchor 100. Instruments for performing rod reduction, derotation, set screw insertion, or other surgical steps can be inserted through or coupled to the instrument body 200. For example, a reduction instrument 300 can be coupled to the instrument body 200 and can be used to urge a rod into a rod seat of the bone anchor 100. As another example, a derotation instrument 500 can be attached to the reduction instrument 300 to facilitate a derotation maneuver or application of other manipulation forces. A modular driver adapter 350 or a modular handle adapter 400 can be attached to the reduction instrument 300 and/or the derotation instrument 500 to facilitate rod reduction. A set screw or other closure mechanism 602 and an associated driver instrument 604 can be inserted through the derotation instrument 500, the reduction instrument 300, and/or the instrument body 200 to secure the set screw to the receiver member 104 of the bone anchor 100.

Figure 3A:
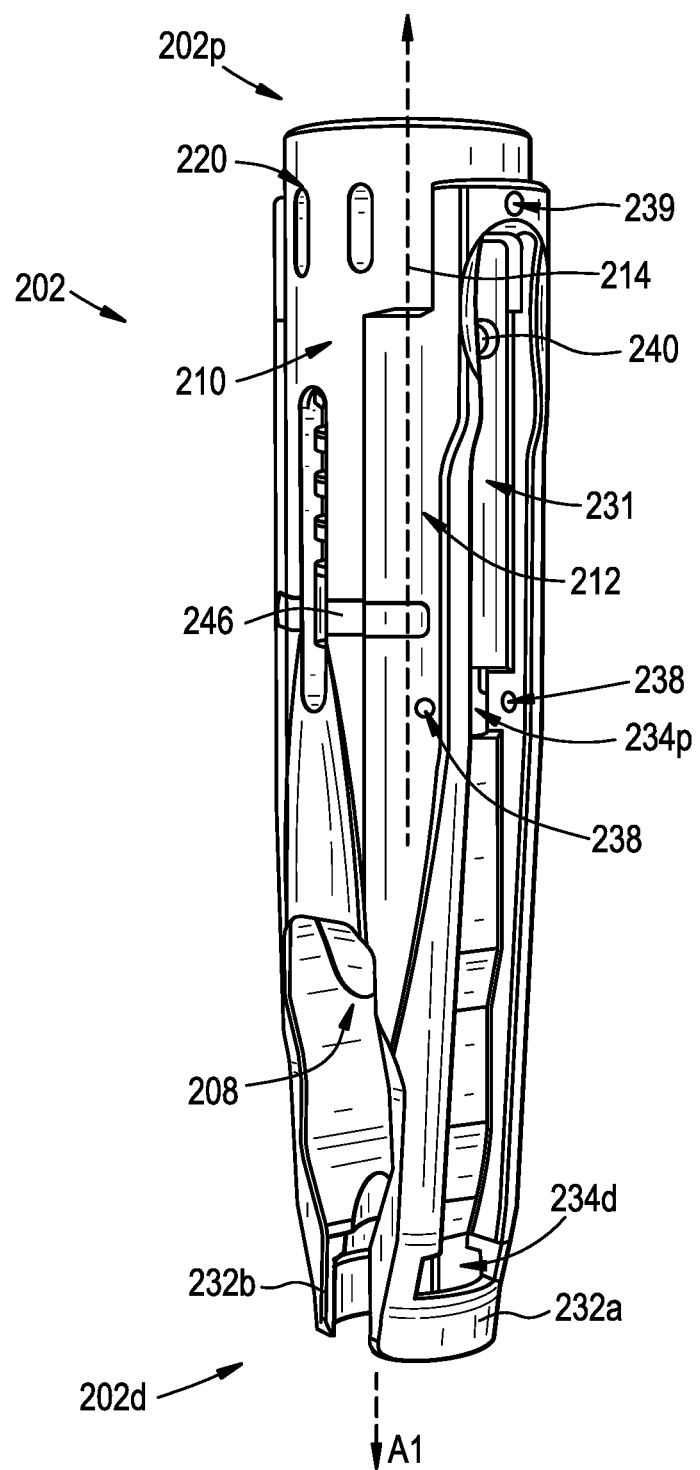
FIG. 3A is a perspective view of a housing of the instrument body of FIG. 2A.
Figure 3B:
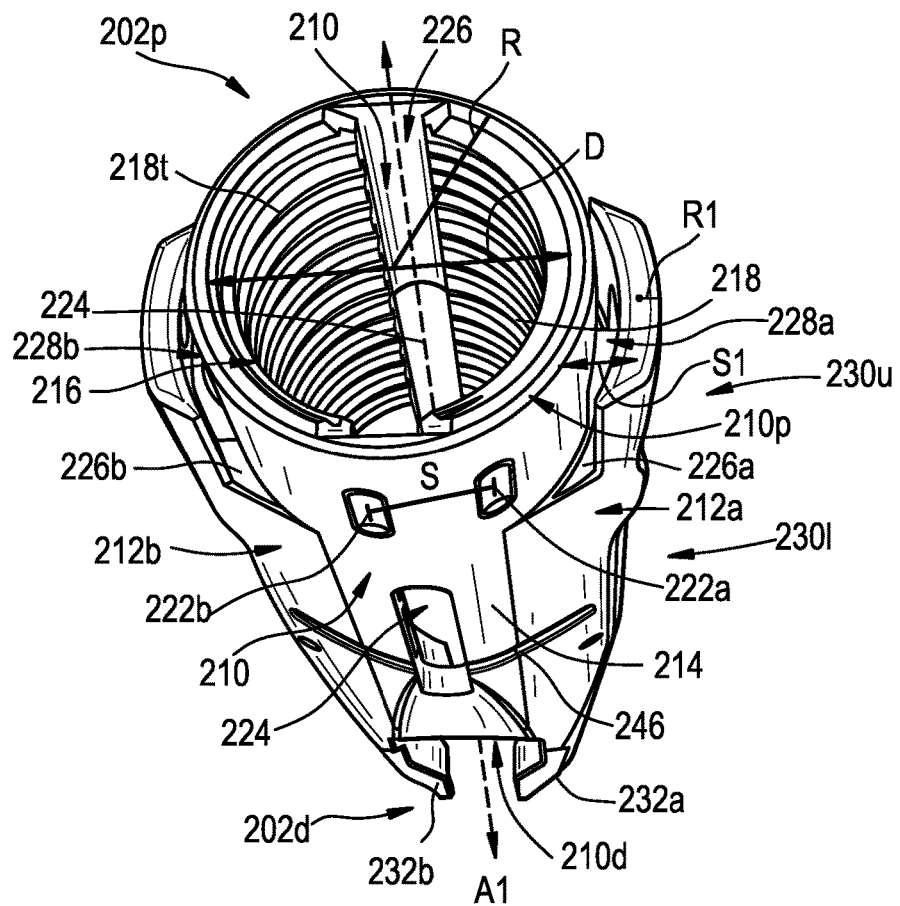
FIG. 3B is another perspective view of the housing of FIG. 3A.
Figure 3C:
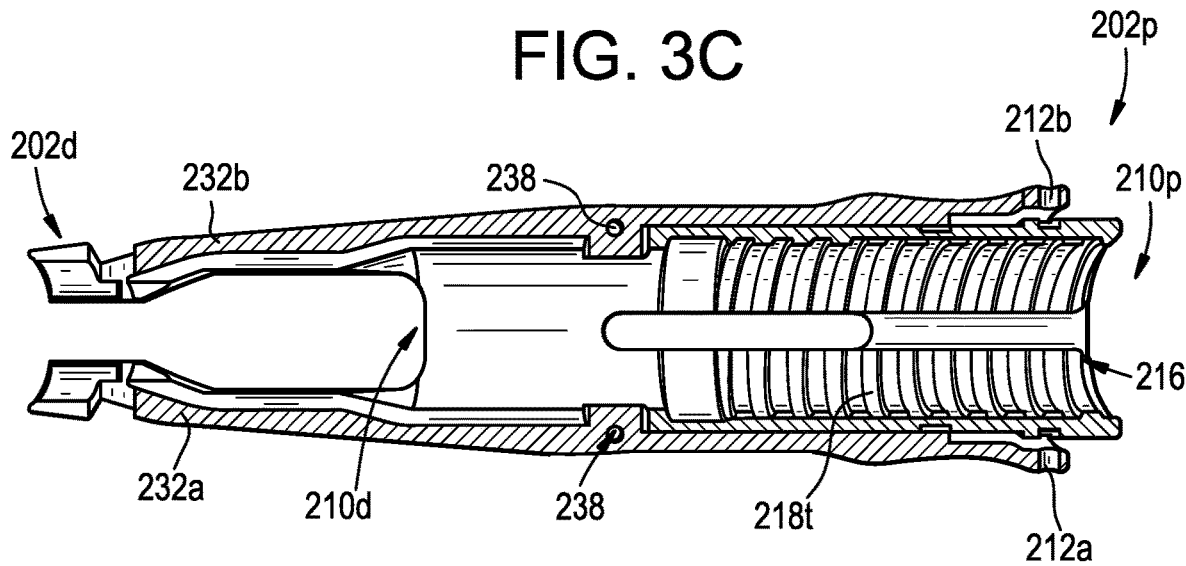
FIG. 3C is a longitudinal sectional view of the housing of FIG. 3A.

The housing 202 of the instrument body 200 is shown in greater detail in FIGS. 3A-3C. The housing 202 can include a generally tubular central portion 210 having opposed wings 212a, 212b extending laterally therefrom and first and second static or fixed arms 232a, 232b extending distally therefrom. The central portion 210 can be defined by a sidewall 214 circumscribing the channel 208. The channel 208 can extend along a central longitudinal axis A1 of the instrument body 200 from a proximal end 202p of the instrument body to a distal end 202d of the instrument body. The channel 208 can define a diameter D through which instruments, implants, or other objects can be inserted. An interior surface of the channel 208 can be threaded or can include other mating features 216 for cooperating with an instrument inserted therethrough, such as a reduction instrument 300, to advance the instrument longitudinally relative to the instrument body 200. The arms 232a, 232b can define a rod slot therebetween. Recesses 231 for receiving the pivoting arms 206 can be defined in the wings 212 and/or in the fixed arms 232. The recesses 231 can be open to the rod slot adjacent a distal end thereof to allow the pivoting arms 206 to selectively pass through the fixed arms 232 to engage a bone anchor 100 disposed therebetween. The locking member or locking ring 204 can be disposed between the central portion 210 and the wings 212, and can be rotated between a first position, in which the locking member blocks the arms 206 from pivoting and a second position in which the locking member does not block the arms from pivoting.

The sidewall 214 can include a mating feature 216 for mating the reduction instrument 300 or other instruments to the instrument body 200. The mating feature 216 can be formed integrally with the sidewall 214, or can be formed as a separate sleeve or insert disposed within the sidewall. While a threaded mating feature 216 is shown, it will be appreciated that any of a variety of other mating features can be used instead or in addition, such as gears, levers, posts, wedges, and the like. The mating feature 216 can include a threaded surface 218t that can engage a threaded portion of an instrument, e.g., a threaded portion of the reducer shaft 300, inserted therethrough. The threaded engagement between the instrument body 200 and the reduction instrument 300 can provide mechanical advantage in advancing the reduction instrument distally within the instrument body to reduce a spinal rod.

The central portion 210 can include one or more tracks 224. The tracks 224 can be formed as throughholes in the sidewall 214 of the central portion 210. Each track 224 can be located between the wings 212a, 212b on the sidewall 214 of the central portion 210 as shown, or can be located on or along the wings 212a, 212b. The track 224 can receive an ear or protrusion of an instrument inserted through the body 200 to maintain the instrument, or a portion thereof, at a fixed rotational position relative to the housing 202. The track 224 can allow a user to observe a distance which an instrument has traveled through the housing 202.

The locking member 204 can be coupled to a proximal end 210p of the central portion 210. For example, the wings 212 can be spaced apart from the central portion 210 by a distance S1 adjacent a proximal end thereof to define opposed seats in which the locking member 204 can be rotatably disposed. An outer sidewall 214 of the central portion 210 can include one or more recesses 222a, 222b for maintaining the locking member 204 in locked or unlocked positions. The recesses 222a, 222b can be spaced apart a distance S from one another. The recesses 222a, 222b can be configured to receive a mating tab 254 of the locking member 204 to lock a rotational position of the locking member 204 relative to the housing 202, as discussed further below. The distance S between the recesses 222a, 222b can correspond to a distance that the locking member 204 can be rotated to switch the instrument body 200 from an unlocked position to a locked position.

Each wing 212a, 212b can extend laterally from the central portion 210. The wings 212a, 212b can include proximal-facing abutment surfaces 226a, 226b that support the locking member 204. The abutment surfaces 226a, 226b can extend continuously about the circumference of the central portion 210, or can be separated by gaps 228a, 228b as shown. The abutment surfaces 226a, 226b can be configured to support rotation of the locking member 204, as discussed further below.

Each wing 212 can include a lower portion 230l and an upper portion 230u. The abutment surface 226 can define the division between the lower portion 230l and the upper portion 230u. The lower portion 230l can be integrally formed with the central portion 210, though in some embodiments, the lower portion 230l and the central portion 210 can be separate components coupled by snap-fit, press-fit, adhesives, welding, or other attachment techniques.

The lower portion 230l can extend distally from the abutment surface 226 around the central portion 210. As shown, the lower portion 230l can extend distal to the distal-most end of the central portion 210 to include the fixed arms 232a, 232b. The fixed arms 232a, 232b can be configured to receive a bone anchor assembly 100 therebetween, as discussed further below.

The upper portion 230u can protrude proximally from the abutment surface 226. As shown, the upper portion 230u can include a rounded profile having a radius of curvature R1 that follows or is concentric with a radius of curvature R of the central portion 210. The upper portion 230u can be spaced a distance S1 from the central portion 210 to allow the locking member 204 to be disposed and travel therebetween.

The wing 212 can include a recess or indentation 231 for receiving a pivoting arm 206 therein. As shown, the indentation 231 can extend through the upper portion 230u and the lower portion 230l, though, in some embodiments, the indentation 231 can be limited to the lower portion 230l.

The indentation 231 can include one or more ports or openings 234 therein. The ports 234 can be configured to allow a pivoting arm 206 disposed in the indentation 231 to communicate with the channel 208. In the illustrated embodiment, each indentation 231 can include two ports 234p, 234d. The proximal port 234p can allow the pivoting arm 206 to be coupled to the wing 212. The distal port 234d can be located in the static arm 232 to allow a portion of the pivoting arm 206 to protrude into the channel 208 to couple to the receiver member 104 of the bone anchor assembly 100 disposed between the static arms 232a, 232b.

The central portion 210 and the wings 212a, 212b can include one or more pins 236 for pivotally coupling the arms 206 to the body 202. The pins 236 can be received within corresponding openings 238 located in the wings 212a, 212b to couple the pivoting arm 206 to the wing. The pivoting arms 206 can be movable relative to the housing 202 between open and closed positions. For example, proximal ends of the pivoting arms 206 can be moved towards one another to move distal ends of the pivoting arms away from one another, thereby placing the pivoting arms in an open position in which a bone anchor can be inserted therebetween. The proximal ends of the pivoting arms 206 can be moved away from one another to move the distal ends of the pivoting arms towards one another, thereby placing the pivoting arms in a closed position to clamp, grasp, interlock, or otherwise engage with a bone anchor disposed therebetween.

The housing 202 can include one or more spring receivers 240 therein. The spring receiver 240 can be located in the upper portion 230u to allow a pivot spring or other bias element 242 to be disposed between the pivoting arm 206 and the indentation 231. A force exerted by the bias element 242 can urge the pivoting arm 206 to rotate relative to the housing 202 to secure the bone anchor assembly 100 between the pivoting arms. The bias element 242 can bias the pivoting arms 206 towards the closed position.

The central portion 210 and the wings 212a, 212b can each include openings 239 that are aligned to receive a retaining pin 244 therethrough. The retaining pin 244 can retain the locking member 204 to the housing 202 while allowing the locking member to rotate relative to the housing. The retaining pin 244 can travel within a pin slot or path 260 formed in the locking member 204, as discussed further below.

The instrument body 200 can include one or more depth indicators 246 thereon. The depth indicator 246 can be located on the central portion 210 and/or the wings 212 along a portion of the track 224. The location of the depth indicator 246 can communicate the extent to which an instrument or tool can be advanced through the instrument body 200. For example, when a washer or other marker of the reducer shaft 300 aligns with the depth indicator 246, it can indicate that the reducer shaft is fully advanced within the instrument body 200 such that the rod is fully seated within the bone anchor 100.

Figure 4A:
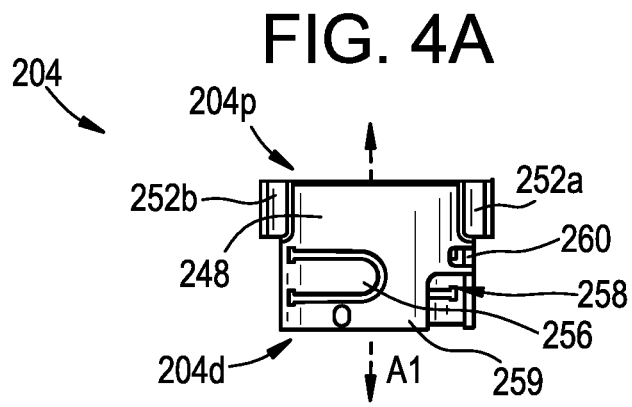
FIG. 4A is a side view of a locking member of the instrument body of FIG. 2A.
Figure 4B:
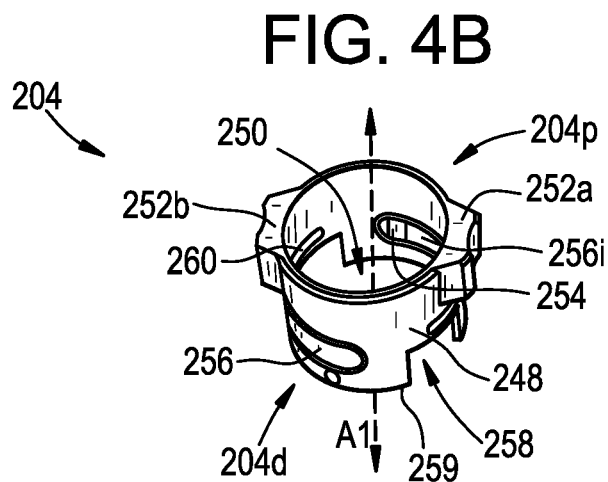
FIG. 4B is a perspective view of the locking member of FIG. 4A.

FIGS. 4A-4B illustrate an exemplary locking member 204. The locking member 204 can include a generally tubular or ring-shaped body defined by a sidewall 248 having a central opening 250. The opening 250 can extend along the axis A1 from a proximal end 204p of the locking member 204 to a distal end 204d of the locking member 204.

The locking member 204 can have a circular shape, as shown, or can have various other shapes, such as oval, oblong, square, rectangular, triangular, and so forth. In some embodiments, the locking member 204 can correspond with a shape of the housing 202 on which it is disposed, or with a shape of an instrument inserted therethrough.

The locking member 204 can include one or more handles or gripping surfaces 252a, 252b extending therefrom. The gripping surfaces 252a, 252b can be fixedly coupled to the locking member 204 such that a force that is exerted on the gripping surfaces 252a, 252b can move the gripping surfaces 252a, 252b and the locking member 204 as a single unit. The gripping surfaces 252a, 252b can allow a user to rotate the locking member 204 to manipulate its orientation.

As noted above, the locking member 204 can include a mating tab 254 that selectively engages the recesses 222 of the housing 202 to maintain the rotational position of the locking member 204 relative to the housing. The mating tab 254 can be a separate component mounted to a spring within the locking member 204 or, as shown, can be formed integrally or monolithically with the locking member 204. For example, the locking member 204 can include a U-shaped circumferential cut-out in the sidewall 248 that defines a cantilevered projection therebetween to form the spring 256. Although a cantilevered projection 256 is shown in the illustrated embodiment, a leaf spring, coil spring, wave spring, non-cantilevered projection, or other bias element can be used instead or in addition. The illustrated locking member 204 includes opposed first and second springs 256, each having a respective mating tab 254 for engaging a respective set of recesses in the housing 202. In other arrangements, the locking member 204 can include fewer or additional springs and mating tabs.

The mating tab 254 can be affixed to an interior portion 256i of the spring 256 such that the mating tab is in communication with the opening 250 of the locking member 204. The mating tab 254 can be a convex or curved protrusion, as shown, or can take other forms, such as a button, a pin, a wedge, and the like. The mating tab 254 can be formed integrally with the spring 256 as shown, though the mating tab can also be a separate component that is welded, threaded, glued, or otherwise coupled to the spring.

The spring 256 can be configured to flex or bend to allow the mating tab 254 to move into and out of engagement with recesses formed in the housing 202, as discussed further below. For example, the mating tab 254 can be received in the recesses 222 of the central portion 210 to prevent the locking member 204 from rotating until a force sufficient to overcome the spring force and disengage the mating tab 254 from the recess 222 is applied to the locking member. The spring 256 can bias the mating tab 254 radially inward towards the opening 250 of the locking member 204.

The locking member 204 can include one or more relief areas 258 therein. As shown, each relief area 258 can be defined by a cut-out in the sidewall 248 of the locking member 204. The relief area 258 can be configured to receive a portion of the pivoting arms 206a, 206b therein when the pivoting arms 206a, 206b are in the open position. The relief area 258 can accommodate for movement of the pivoting arms 206a, 206b to allow the pivoting arms to opened to receive a bone anchor, e.g., a receiver member 104 of the bone anchor, therebetween. The locking member 204 can include one or more blocking portions 259. The blocking portions 259 can be defined by a section of the sidewall 248 circumferentially-adjacent to the relief areas 258. When the blocking portions 259 are aligned with the pivoting arms 206, they can prevent the pivoting arms from opening, thereby locking a bone anchor therebetween.

The locking member 204 can include one or more pin paths 260 therein. The pin paths 260 can be defined as circumferential cut-outs in the locking member 204 that can receive the retention pin 244 therethrough. The retention pin 244 can travel through the pin path 260 as the locking member 204 is rotated relative to the housing 202 to move the instrument body 200 between the locked and unlocked positions. Although two pin paths 260 are shown, it will be appreciated that the locking member 204 can include one or three or more pin paths therein.

Figure 5:
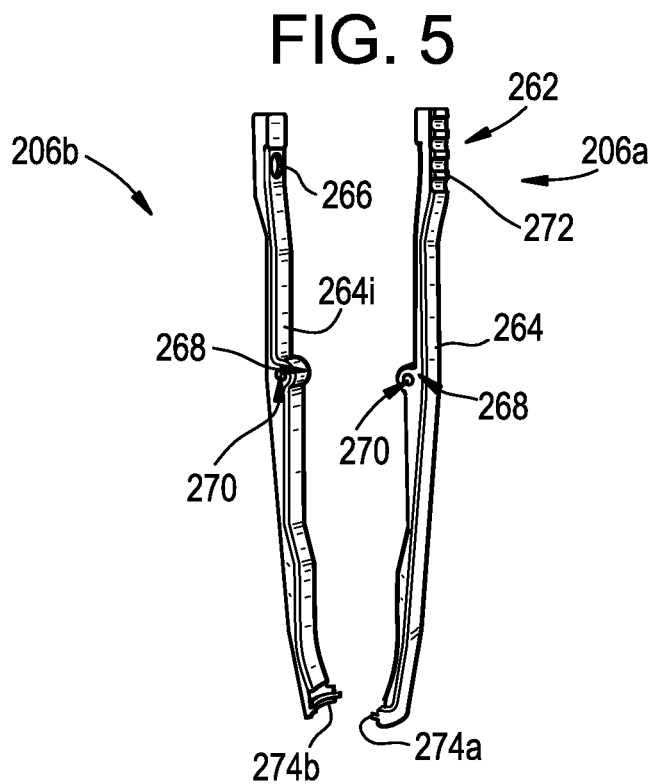
FIG. 5 is a perspective view of pivoting arms of the instrument body of FIG. 2A.

FIG. 5 illustrates the pivoting arms 206a, 206b of the instrument body 200. Each pivoting arm 206 can include a head 262 and a body 264. The head 262 can define a spring seat 266 for receiving the bias element 242, which can be disposed between the pivoting arm 206 and the housing 202. The body 264 can include a hinge 268 having an opening 270 therein configured to receive the pivot pin 236 to couple the pivoting arm 206 to the housing 202. The hinge 268 can be located on an intermediate portion of the body 264, as shown, though the location of the hinge 268 can vary along the length of the body 264.

The head 262 can include a ridged or textured portion 272 on an outer surface of the pivoting arms 206a, 206b. The ridged portions 272a, 272b can facilitate grasping by a user to move the pivoting arms 206a, 206b relative to one another and the housing. For example, grasping the ridged portions 272a, 272b to move the heads 262 of the pivoting arms 206a, 206b closer to one another can move the distal portion of the body 264 of the pivoting arms 206a, 206b radially-outward relative to the axis A1 to release an object, e.g., a bone anchor assembly 100, that is disposed therebetween.

The body 264 can include one or more fingers 274 that can be configured to grasp the receiver member 104 of the bone anchor assembly 100. As shown, the finger 274 can be located on a distal portion of the body 264, though the finger 274 can be located anywhere along the body. The finger 274 can be positioned such that it extends from an interior surface of the body 264i. As shown, the finger 274 can extend substantially perpendicularly to the body, though, in some embodiments, the finger 274 can extend at an angle relative to the body 264 to couple to bone anchor assemblies having different mating geometries. The finger 274 can have an arcuate shape as shown, or can have various other shapes, such as rectangular, oval, oblong, square, circular, triangular, and so forth. In some embodiments, the shape of the finger 274 can vary based on the counterpart mating geometry of a bone anchor assembly with which the instrument body 200 is to be used.

The finger 274 can engage a corresponding groove, surface, or other feature of the bone anchor assembly 100 to secure the bone anchor assembly to the instrument body 200, e.g., such that the instrument body is maintained at a fixed position and orientation with respect to the bone anchor or a receiver member thereof. For example, the fingers 274a, 274b of each pivoting arm 206a, 206b can engage a groove or "top notch" feature of the receiver member 104 of the bone anchor assembly 100 to dock the instrument body 200 thereto. It will be appreciated that the fingers 274a, 274b can engage the bone anchor assembly 100 in either of the locked or unlocked positions of the locking member 204. Accordingly, the instrument body 200 can be docked to a bone anchor even when unlocked, e.g., due to the bias force applied by the springs 242.

In use, the pivoting arms 206a, 206b can be received in the indentations 231a, 231b of the wings 212a, 212b. The bias element 242 can be disposed between the pivoting arms 206a, 206b and the housing 202 to exert a force on the heads 262a, 262b of the pivoting arms 206a, 206b to bias the pivoting arms 206a, 206b towards the closed position. For example, a first end of the bias element 242 can be received in the spring seat 266 of the pivoting arm. A second end of the bias element 242 can be disposed in the spring receiver 240 to dispose the bias element 242 between the housing 202 and the head 262 of the pivoting arms 206a, 206b. The pivoting arms 206a, 206b can be free to move relative to the housing 202 when the locking member 204 is in the unlocked position, and can be constrained from moving relative to the housing when the locking member 204 is in the locked position, as discussed further below. While a coil spring 242 is shown, it will be appreciated that various other bias elements can be used instead or in addition, such as leaf springs, wave springs, torsion springs, resilient compressible members, etc.

Figure 6A:
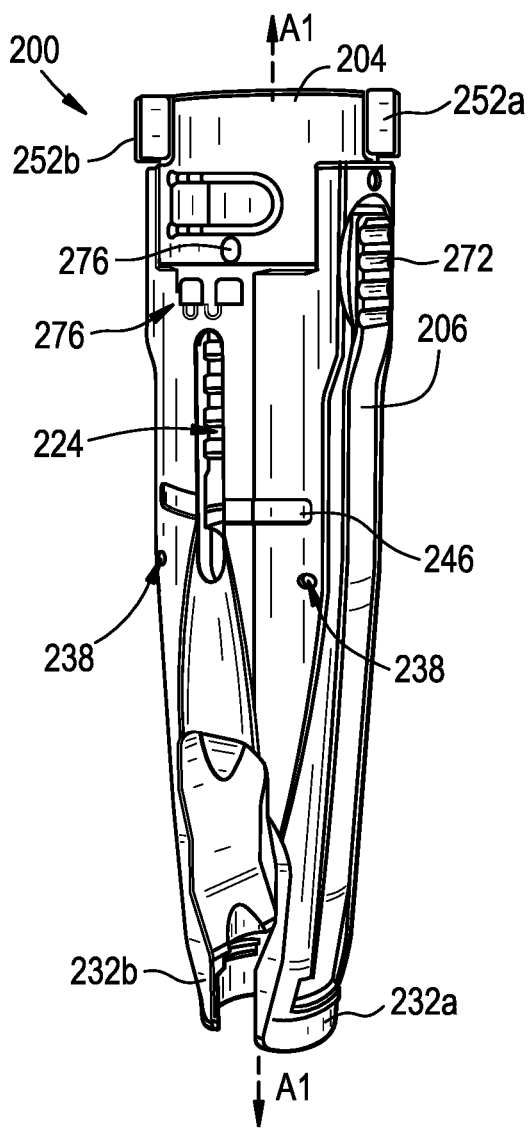
FIG. 6A is a perspective view of the instrument body of FIG. 2A, shown in an unlocked position.
Figure 6B:
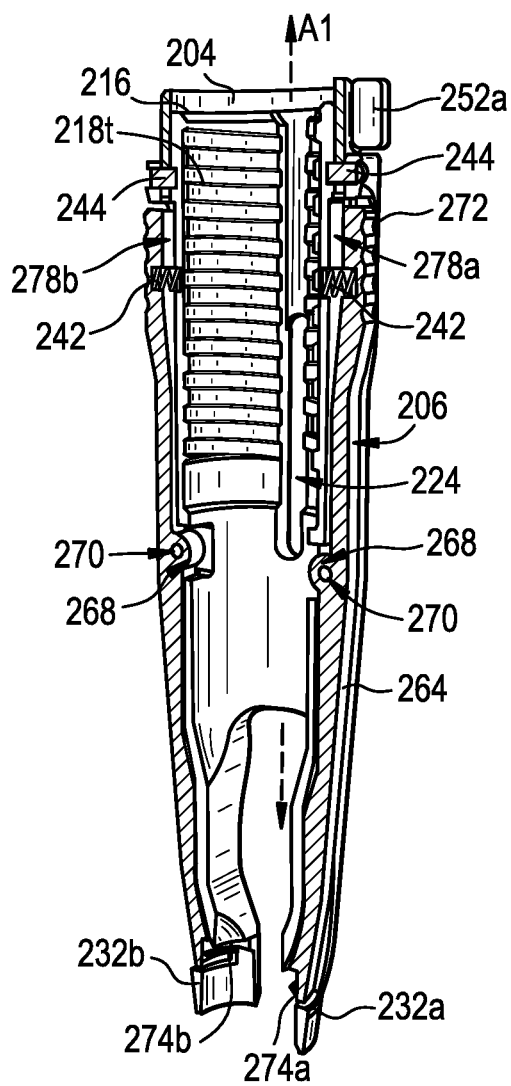
FIG. 6B is a longitudinal sectional perspective view of the instrument body of FIG. 2A, shown in the unlocked position.
Figure 6C:
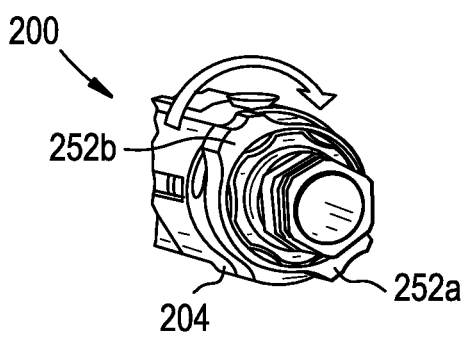
FIG. 6C is a perspective view of the instrument body of FIG. 2A, schematically illustrating movement of a locking member thereof to a closed position.
Figure 6D:
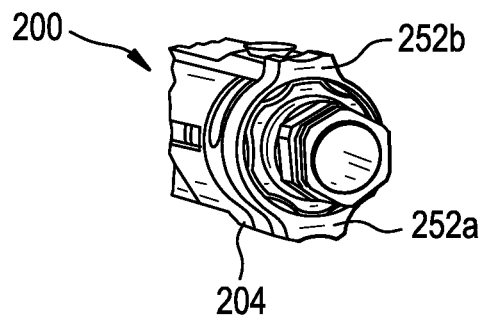
FIG. 6D is a perspective view of the instrument body of FIG. 2A, shown in the closed position.
Figure 6E:
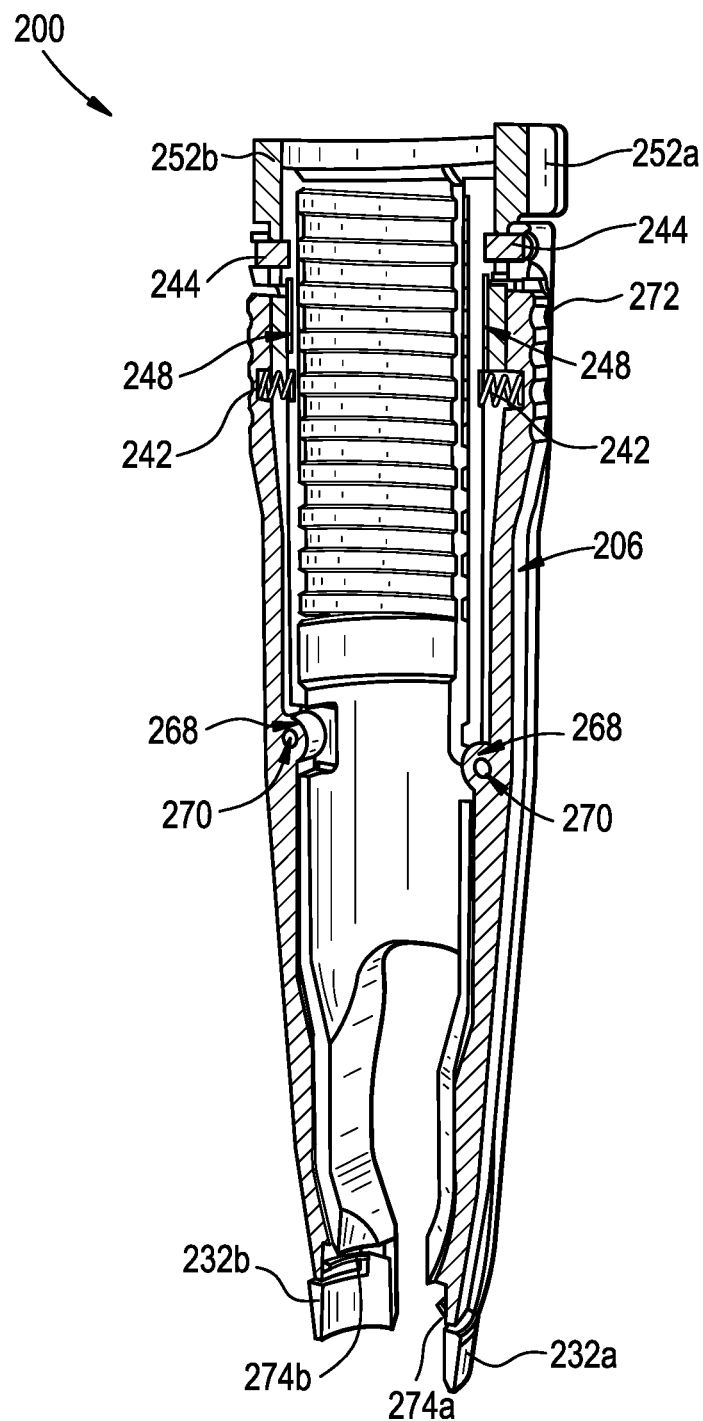
FIG. 6E is a longitudinal sectional perspective view of the instrument body of FIG. 2A, shown in the closed position.

FIGS. 6A-6C illustrate the instrument body 200 in the unlocked position and FIGS. 6D-6E illustrate the instrument body in the locked position. The locking member 204 can be rotated to move the instrument body 200 between (i) an unlocked position in which the pivoting arms 206a, 206b are free to pivot relative to the housing 202 between open and closed positions of the arms, and (ii) a locked position in which the pivoting arms 206a, 206b are constrained from pivoting relative to the housing 202 by the position of the locking member 204 to limit or prevent relative movement therebetween, thereby maintaining the arms in the closed position.

The instrument body 200 can include indicators 276 that show whether the instrument is in the unlocked position or in the locked position. For example, as shown in FIG. 6A, the instrument body 200 can include labels or images thereon to indicate the position of the locking member 204. The instrument body 200 can include a first image of a padlock in an unlocked or open position that can be aligned with the first recess 222a and a second image of a padlock in a locked or closed position that can be aligned with the second recess 222b. The locking member 204 can have a circle, as shown, an arrow, or another mark thereon that can align with, or point to, one of the images on the instrument body 200. It will be appreciated other images can be used instead or in addition, such as text labels, e.g., that read "open" and "closed," respectively, other drawings, and the like.

The instrument body 200 can include additional indicators for communicating the position of the instrument body. For example, a position of the gripping surfaces 252a, 252b relative to the wings 212a, 212b can inform the user as to whether the locking member 204 is in the unlocked position or in the locked position.

FIGS. 6A-6C illustrate the instrument body 200 with the locking member 204 in the unlocked position. As shown, the gripping surfaces 252a, 252b of the locking member 204 are rotationally offset from the pivoting arms 206, which can indicate that the instrument body 200 is in the unlocked position. The circle image 276 of the locking member 204 is aligned with the image of the padlock in the unlocked position, which can also indicate that the locking member 204 is in the unlocked position.

In the unlocked position, the pivoting arms 206a, 206b are free to rotate relative to the housing 202, e.g., between the open and closed positions of the arms. The pivoting arms 206a, 206b are not constrained and the fingers 274a, 274b are free to move between engaging and disengaging an implant or other object, e.g., a bone anchor assembly 100, that is disposed therebetween. For example, the pivoting arms 206a, 206b can be applied to the bone anchor assembly 100 to secure the bone anchor assembly therebetween by inserting the fingers 274a, 274b into a groove or other mating feature of the bone anchor assembly. In the unlocked position, exerting a force on the heads 262a, 262b of the arms can release the arms 206a, 206b from the bone anchor assembly 100.

As shown in FIG. 6B, the relief area 258 of the locking member 204 can be rotationally aligned with the head 262 of the pivoting arm 206, such that the locking member does not block movement of the arm and such that the head 262 of the arm is free to move radially-inward and radially-outward relative to the axis A1. That is, in the unlocked position, the relief areas 258 can define voids 278a, 278b aligned between the heads 262a, 262b and the central portion 210, thereby allowing the pivoting arms 206a, 206b to move relative to the housing 202 by exerting a force on the heads 262a, 262b to overcome the force of the bias element 242.

The locking member 204 can be rotatable relative to the central portion 210 about the axis A1 to move between an unlocked position and a locked position. As shown in FIG.

6C, the locking member 204 can be rotated in a clockwise direction, when viewed from a proximal perspective, to move the locking member 204 into the locked position, though, in other embodiments, the direction of rotation can be reversed. As a rotational force is imparted onto the locking member 204, the force can overcome a resistance between the mating tab 254 and the first recess 222a to remove the mating tab 254 from the first recess 222a. The mating tab 254 can travel along the central portion 210 as the locking member 204 is rotated.

As the locking member 204 rotates, the one or more retention pins 244 can travel from a first end of the pin path 260 towards a second end of the pin path 260. As the retention pins 244 approach the second end of the pin path 260, the mating tab 254 can move along the surface of the central portion 210. Once the mating tab 254 is aligned with the second recess 222b, the bias of the spring 256 can move the mating tab 254 into the second recess 222b, thereby preventing further rotation of the locking member 204. The mating tab 254 can be received in the second recess 222b to prevent further rotation of the locking member 204 with respect to the housing 202 and to maintain the locking member 204 in the locked position. Further rotation of the locking member 204 can also be prevented by the pin path 260, which can restrict further travel of the retention pin 244 therein.

FIGS. 6D-6E illustrate the instrument body 200 with the locking member 204 in the locked position. As shown, the mating tab 254 can be disposed in the second recess 222b and the gripping surface 252 of the locking member 204 can be aligned with the pivoting arms 206. In the locked position, the blocking portions 259 of the locking member 204 can be positioned between the head 262 of the pivoting arm 206 and the central body 210. That is, in the locked position, the blocking portion 259 of the locking member 204 can block the head 262 of the pivoting arm 212 from moving relative to the housing 202, e.g., from pivoting radially-inward towards the axis A1. Accordingly, the arms 206a, 206b can be prevented from pivoting out of engagement with an implant or other object captured therebetween, e.g., a bone anchor assembly 100.

While the illustrated locking member 204 rotates about the axis A1 to move between the locked and unlocked positions, it will be appreciated that other arrangements are possible instead or in addition. For example, the locking member 204 can be a ring configured to slide axially along the housing 202 between a first position in which a blocking portion of the locking member is disposed between the arms 206 and the central body 210 to prevent the arms 206 from pivoting and a second position in which the locking member is not disposed between the arms 206 and the central body 210, such that the arms 206 are free to pivot.

As noted above, the instrument body 200 can be used with any of a variety of other instruments. FIGS. 7A-7F illustrate an exemplary reduction instrument or reducer shaft 300 that can be used with the instrument body 200.

The reducer shaft 300 can include a generally cylindrical shaft having a proximal end 300p and a distal end 300d with an inner lumen or working channel 302 passing therethrough. The reducer shaft 300 can have an outside diameter D1 that is smaller than the diameter D of the channel 208 such that the reducer shaft 300 can be inserted through the channel 208 of the instrument body 200. In operation, at least a portion of the reducer shaft 300 can rotate relative to the instrument body 200 about the axis A1 to advance the reducer shaft 300 distally relative to the instrument body and a bone anchor 100 secured thereto, thereby urging a rod towards a rod seat of the bone anchor. The reducer shaft 300 can include a proximal portion 304 configured to rotate relative to the instrument body 200 and a distal portion 306 configured to remain at a fixed rotational position relative to the instrument body. The fixed rotational position can be one in which opposed arms of the distal portion 306 are aligned with the rod slot defined between the fixed arms 232 of the instrument body 200. The reducer shaft 300 can be cannulated or can define a working channel therethrough, e.g., to allow the reducer shaft 300 to be inserted over a guidewire or to allow instruments, implants, or other objects to be inserted through the reducer shaft. For example, the reducer shaft 300 can allow a set screw or other closure mechanism, and an instrument for applying the set screw or closure mechanism to a bone anchor, to be passed through the lumen 302 to apply the set screw or closure mechanism to the receiver member 104 of a bone anchor assembly 100 to which the instrument body 200 is docked.

The proximal portion 304 can include a drive interface 308 to facilitate application of torque or other forces to the reducer shaft 300, e.g., for advancing the reducer shaft along threads 216 of the instrument body 200 during rod reduction. The drive interface 308 can have any geometry that facilitates application of torque or other forces to the reducer shaft 300, such as a hex drive 310 as shown. The drive interface 308 be received in or otherwise coupled to an instrument to impart a driving force onto the proximal portion 304. The drive interface 308 can include a groove 312 therein to facilitate mating of the reducer shaft 300 to other instruments, as described further below.

The proximal portion 304 can include a flange or shoulder 314 to limit the degree to which the proximal portion 304 can be received within a counterpart drive interface of an instrument, as described further below. The shoulder 314 can have a diameter D3 that is larger than the diameter D2 of adjacent portions of the reducer shaft 300

The proximal portion 304 can include an exterior thread 316 configured to mate with the threaded surface 218t of the instrument body 200.

The proximal portion 304 can include a coupling 318 for attaching the proximal portion 304 to the distal portion 306. The coupling 318 can be configured to attach the proximal and distal portions 304, 306 to prevent relative longitudinal translation therebetween while still allowing free rotation of the proximal portion 304 relative to the distal portion 306 about the axis A1. As shown, the coupling 318 can include one or more flexible and resilient arms 320a, 320b defined by cut-outs formed in the distal end of the proximal portion 304. Opposed tabs 322a, 322b can be defined between the arms 320. In use, the arms 320 can be deflected radially inward as the proximal portion 304 is inserted into the distal portion 306. Once inside the distal portion 306, the arms 320a, 320b can return towards their resting position to engage a circumferential groove 323 formed in an interior surface 306i of the distal portion, thereby coupling the proximal portion 304 to the distal portion.

The reducer shaft 300 can include a groove 324 for receiving a washer 326. The washer 326 can serve as a visual indication as to the degree to which the reducer shaft 300 has been advanced relative to the instrument body 200.

The distal portion 306 of the reducer shaft 300 can be defined as a generally tubular member. The diameter of the distal portion 306 can reduce or taper from a larger proximal diameter D4 to a smaller distal diameter D5. The distal portion 306 can include one or more arms 334a, 334b extending distally therefrom. The arms 334 can be configured to contact and bear against a spinal rod to urge the rod distally as the reducer shaft 300 is translated distally within the instrument body 200. The distal contact surfaces of the arms 334 can be shaped to match a rod with which the reducer shaft 300 is to be used. For example, the arms 334 can include circular cut-outs having a diameter commensurate with the rod diameter. The arms 334 can be aligned with the rod slot defined between the fixed arms 232 of the instrument body 200. The arms 334 can define spaces therebetween through which the pivoting arms 206 of the instrument body 200 can pass to engage a bone anchor or other object. The arms 334 can be rotationally offset from the fixed and pivoting arms 232, 206 of the instrument body 200, such that the arms 334a, 334b can advance distally towards the bone anchor assembly 100 when the reducer shaft 300 is advanced through the instrument body 200 without interfering with the engagement between the pivoting arms 206a, 206b and the bone anchor assembly 100. Though two arms 334a, 334b are shown, the reducer shaft 300 can include any number of rod-engaging arms.

The distal portion 306 can include one or more ears or projections 335 extending radially-outward therefrom. The projections 335 can be received within the tracks or slots 224 of the instrument body 200 to maintain the distal portion 306 at a fixed rotational position relative to the instrument body 200 about the axis A1. Engagement between the projections 335 and the slots 224 can maintain the arms 334 in alignment with the rod slot. In other arrangements, the position of the projections and the slots can be reversed, with the instrument body 200 including one or more projections received within slots formed in the distal portion 306.

Figure 7A:
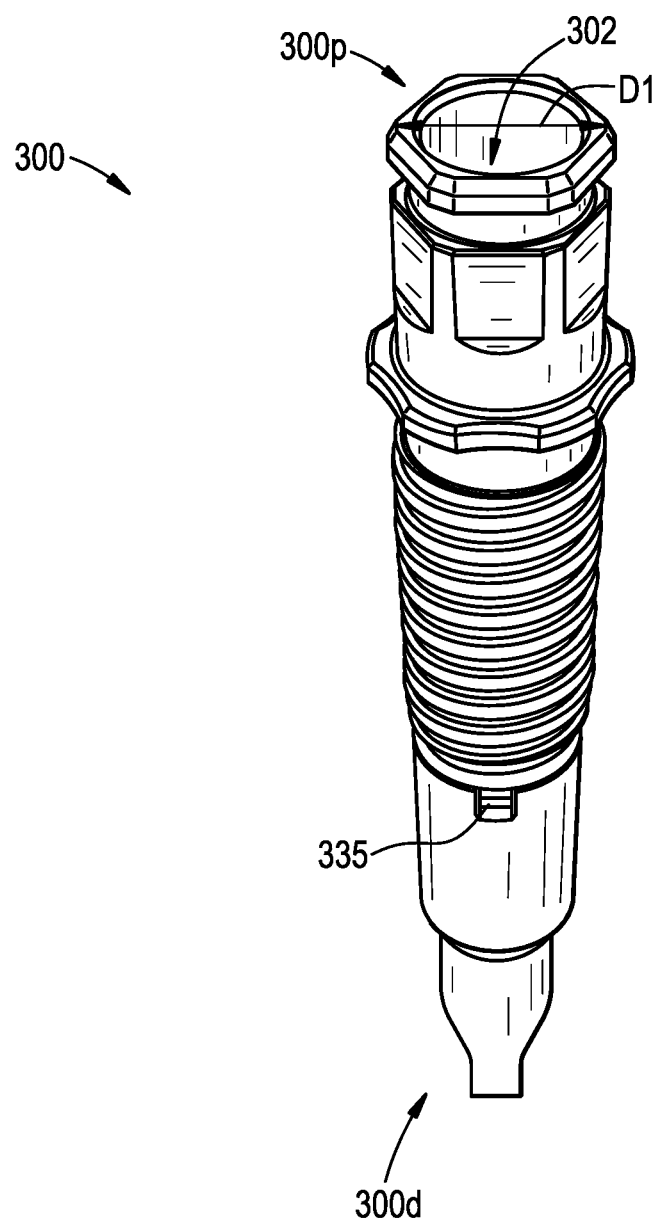
FIG. 7A is a perspective view of a reducer shaft.
Figure 7B:
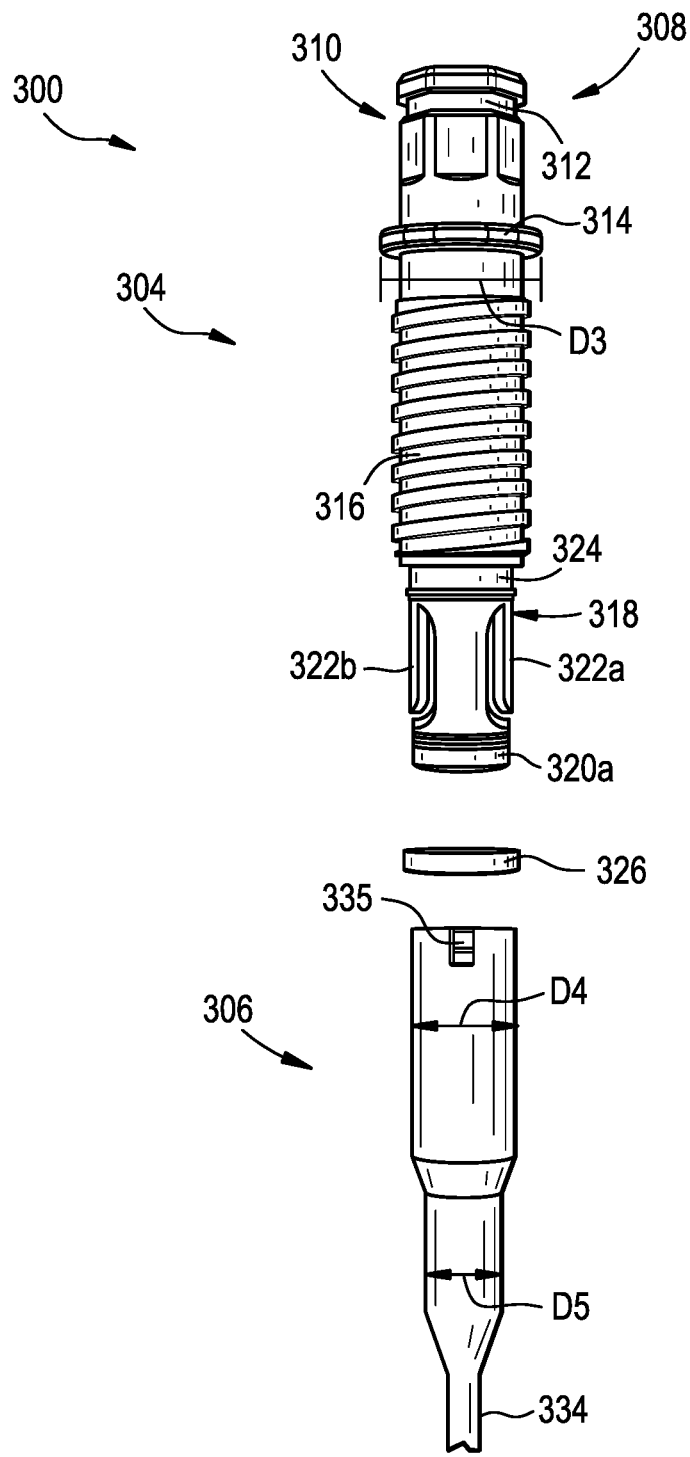
FIG. 7B is an exploded side view of the reducer shaft of FIG. 7A.
Figure 7C:
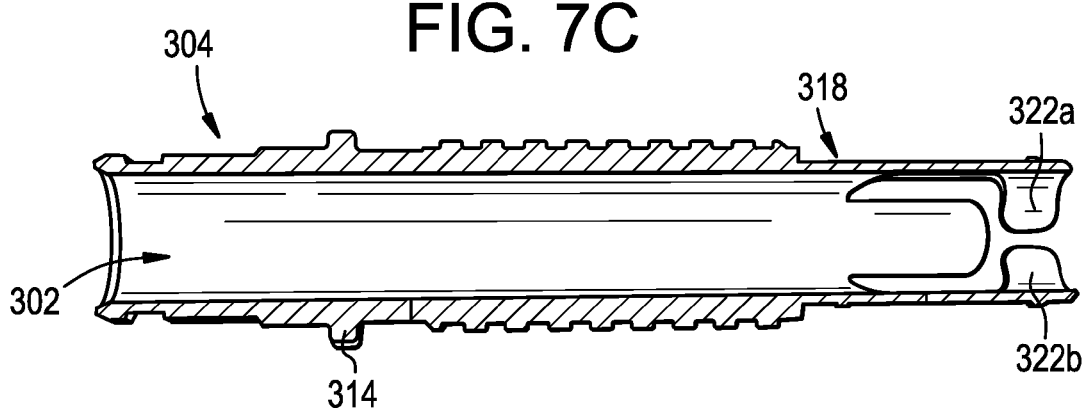
FIG. 7C is a longitudinal sectional view of a proximal portion of the reducer shaft of FIG. 7A.
Figure 7D:
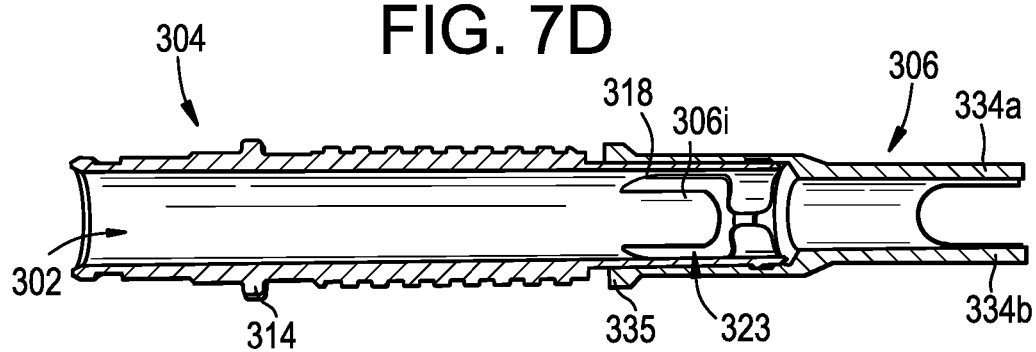
FIG. 7D is a longitudinal sectional view of the reducer shaft of FIG. 7A.
Figure 7E:
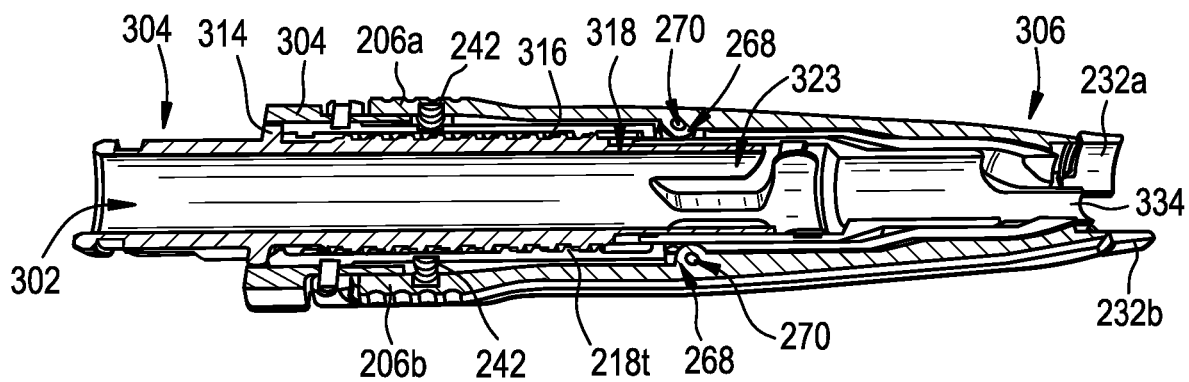
FIG. 7E is a longitudinal sectional view of the instrument body of FIG. 2A having the reducer shaft of FIG. 7A disposed therein.
Figure 7F:
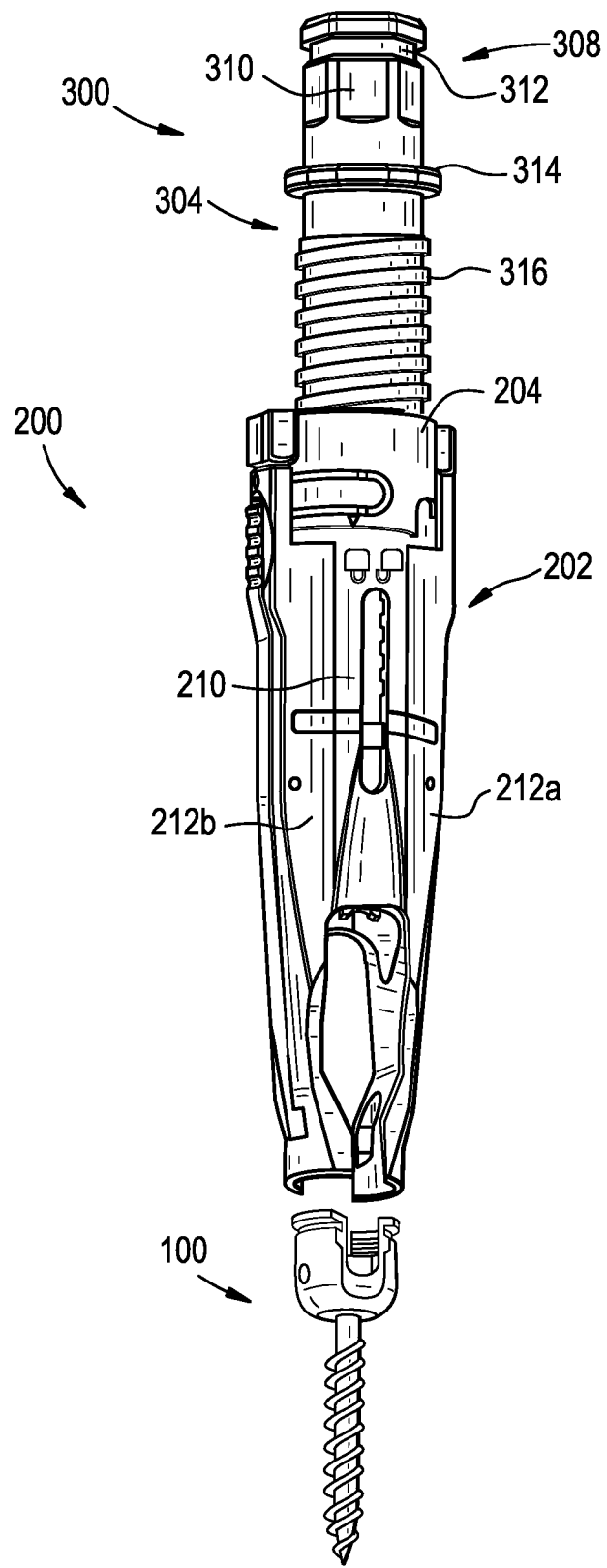
FIG. 7F is a perspective view of the instrument body of FIG. 2A, shown with the reducer shaft of FIG. 7A disposed therein and docked to a bone anchor assembly.

As shown in FIG. 7F, the reducer shaft 300 can be loaded into the instrument body 200 prior to the instrument body 200 being docked to the bone anchor assembly 100. Alternatively, the instrument body 200 can be docked to the bone anchor assembly 100 prior to the reducer shaft 300 being inserted therethrough.

The instrument body 200 can be designed to support both proximal and distal loading of a bone anchor assembly 100. For example, the instrument body 200 can be advanced distally over a bone anchor to position the bone anchor between the arms 232. As another example, the bone anchor can be inserted into the proximal end of the reducer body 200 and advanced distally with respect thereto to position the bone anchor between the arms 232.

Figure 8A:
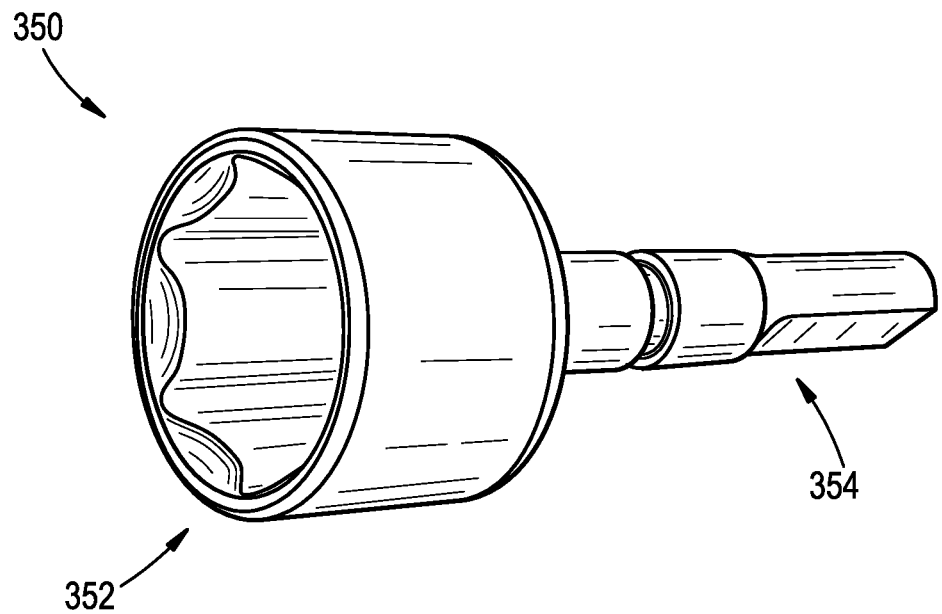
FIG. 8A is a perspective view of an adapter with a modular drive interface.

FIG. 8A illustrates an exemplary adapter 350 that can be coupled to the reducer shaft 300 or to other instruments, such as the derotation instrument 500 described further below. The adapter 350 can facilitate application of torque to an attached instrument. For example, the adapter 350 can allow a modular handle, powered driver, or other tool to be rotationally fixed to the reducer shaft 300 for applying torque to advance or retract the reducer shaft relative to the instrument body 200. The adapter 350 can include a distal drive interface 352 configured to mate with the drive interface of the reducer shaft 300 and a proximal drive interface 354 configured to mate with a modular handle, powered driver, manual, electric, hydraulic, or pneumatic drill or driver tool, or other tools.

Although the drive interface 352 of the adapter 350 is discussed herein as receiving the drive interface 308 of the reducer shaft 300 therein, it will be appreciated that the adapter 350 can receive the drive interface of the derotation instrument 500, and/or various other instruments.

The drive interface 352 of the adapter 350 can be configured to attach to counterpart drive interfaces, e.g., of the reduction instrument 300, without locking thereto. This can allow the adapter 350 to be quickly and easily interchanged between a plurality of different counterpart instruments. For example, a surgeon can quickly and easily move the adapter 350 from a first reduction shaft 300 disposed over a first bone anchor implanted in a patient to a second reduction shaft 300 disposed over a second bone anchor implanted in the patient.

Figure 8B:
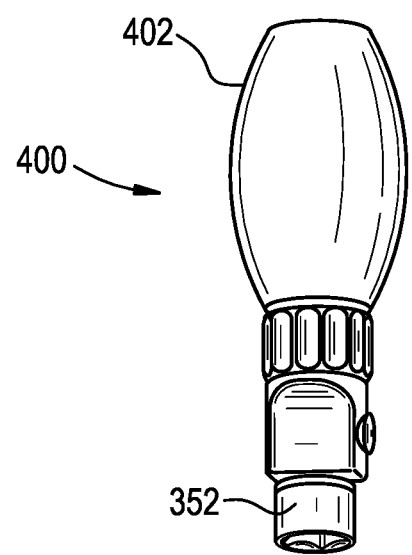
FIG. 8B is a perspective view of an adapter with a handle.

In some embodiments, the proximal drive interface of the adapter 350 can be replaced with a built in handle. For example, FIG. 8B illustrates an exemplary adapter 400 having a distal drive interface 352 and a built-in handle 402.

Figure 8C:
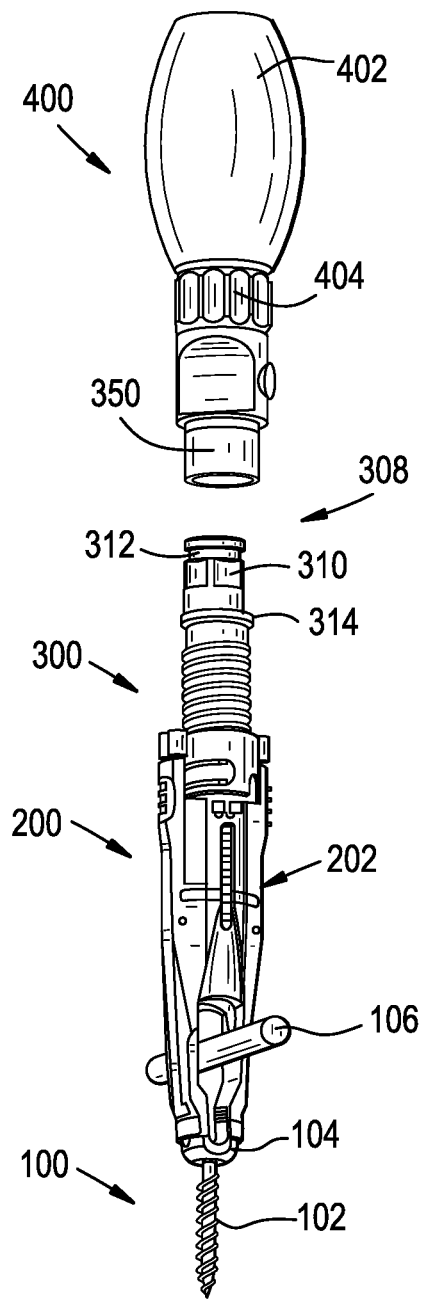
FIG. 8C is a perspective view of the instrument body of FIG. 2A and the reducer shaft of FIG. 7A in use to reduce a spinal rod.
Figure 8D:
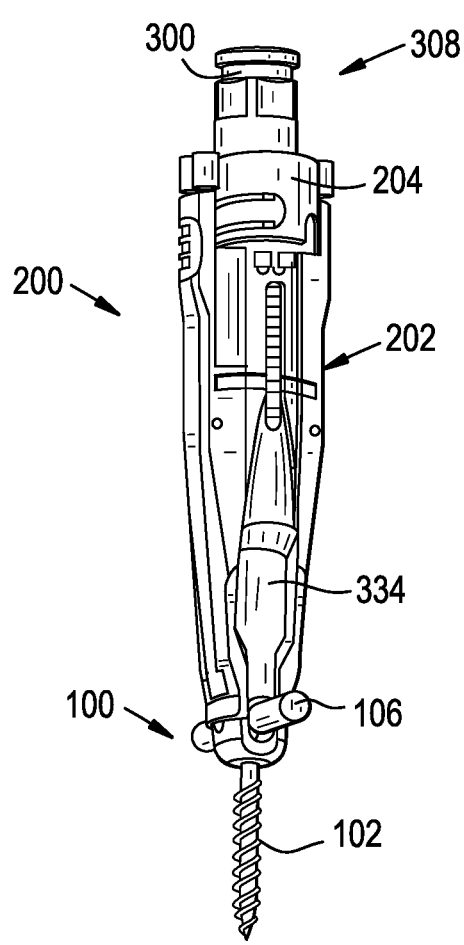
FIG. 8D is another perspective view of the instrument body of FIG. 2A and the reducer shaft of FIG. 7A in use to reduce a spinal rod.

FIGS. 8C-8D illustrate a spinal rod 106 being reduced into the receiver member 104 of a bone anchor assembly 100 using the instrument body 200, the reduction shaft 300, and the adapter 400. The instrument body 200 can be docked to a bone anchor assembly 100 as described above, before or after implanting the bone anchor assembly 100 in a patient. The bone anchor assembly 100 can be driven into bone using a driver instrument inserted through the instrument body 200 while the instrument body is locked to the bone anchor assembly. A spinal rod 106 can be inserted through the rod slot of the instrument body 200 and placed in contact with the distal ends of the arms 334 of a reducer shat 300 inserted through the instrument body. The adapter 400 can be rotated relative to the instrument body 200 to advance the reducer shaft 300 distally and urge the rod 106 into the rod seat of the bone anchor assembly 100.

FIGS. 9A-9I illustrate an exemplary embodiment of a derotation instrument or derotation assembly 500 that can be used with the reducer shaft 300 and/or the instrument body 200 described herein. The derotation assembly 500 can be used to provide additional leverage when manipulating a vertebra or other bone to which the assembly 500 is coupled. For example, the assembly 500 can facilitate application of derotation, distraction, compression, or other forces to a vertebra or to a fixation construct, e.g., to correct a spinal angle, deformity, or other condition of the patient. The derotation assembly 500 can also provide an attachment point for a derotation rack, navigation system, or other surgical instrumentation.

Figure 9A:
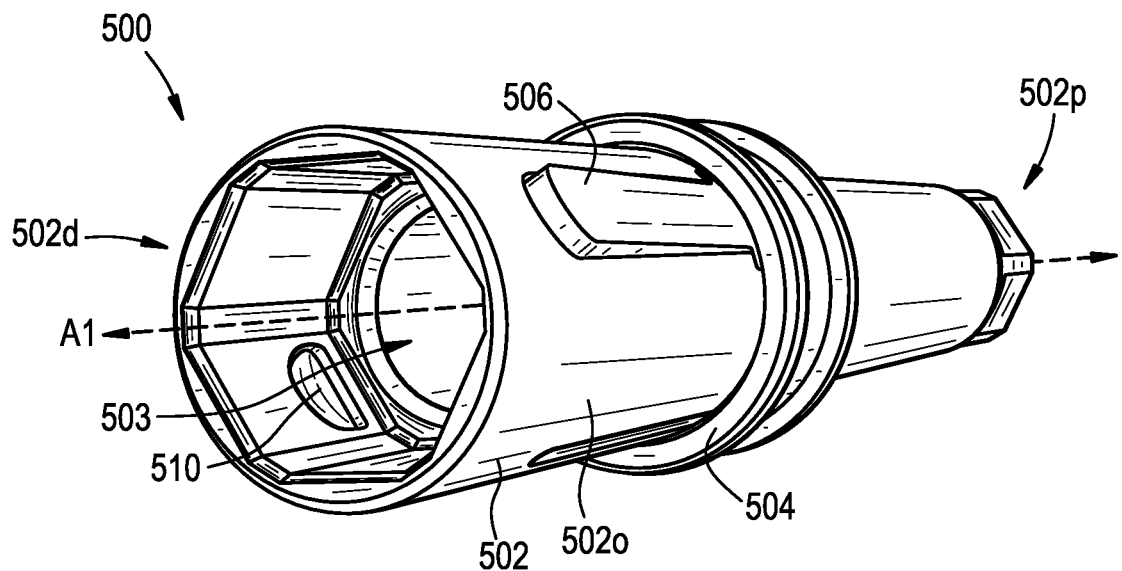
FIG. 9A is a perspective view of a derotation assembly.
Figure 9B:
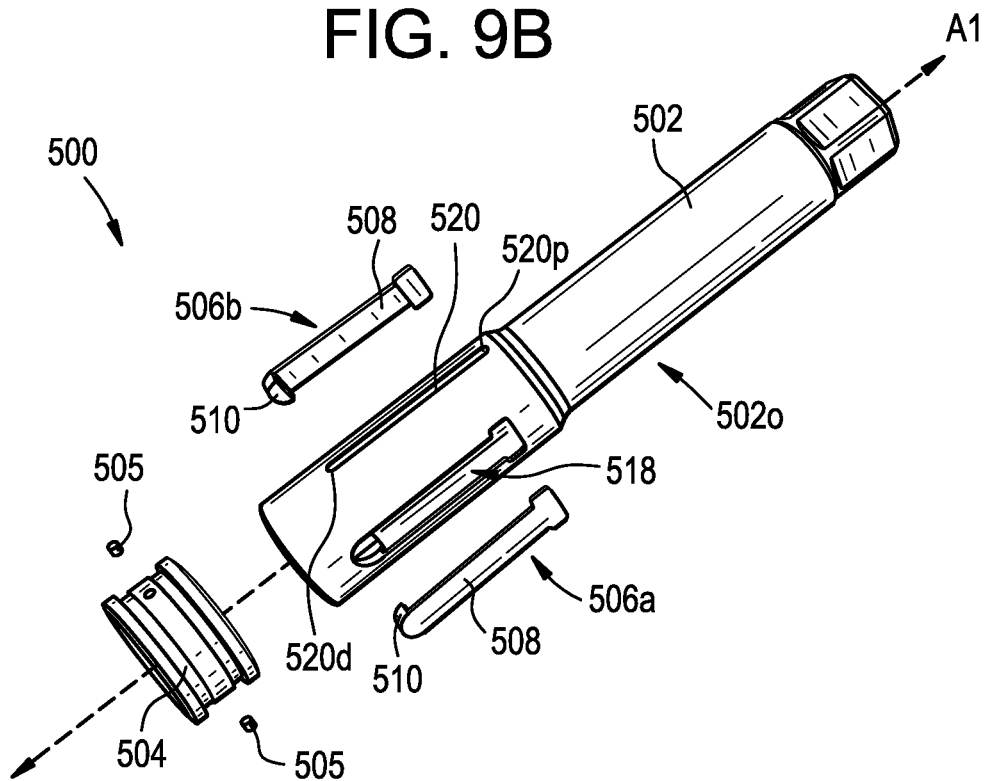
FIG. 9B is an exploded perspective view of the derotation assembly of FIG. 9A.

As shown in FIG. 9B, the derotation assembly 500 can include a tubular shaft 502 having one or more arms 506 for engaging with a reducer shaft 300 or other instrument to secure the assembly 500 thereto. The assembly 500 can include a locking ring 504 for selectively maintaining the arms 506 in engagement with the reducer shaft 300 or other instrument. The shaft 502 can include an interior sidewall that defines a lumen or working channel 503 that extends through the shaft. The locking ring 504 can be disposed around an outer surface 502o of the shaft 502 to move relative thereto. As shown, the locking ring 504 can be coupled to the shaft 502 via one or more pins 505 inserted therethrough. The hinged arms 506 can be configured to grasp a drive interface of an instrument inserted therethrough. The hinged arms 506 can be movable between an open configuration in which an instrument can be inserted and removed from the shaft 502 and a closed position in which an instrument is captured or retained within the shaft. The locking ring 504 can be disposed in an unlocked position in which the hinged arms 506 are free to move, or pivot, relative to the shaft 502 and a locked position in which the hinged arms 506 are constrained from moving relative to the shaft 502. The hinged arms 506 can pivot radially-inward and/or radially-outward relative to the axis A1. The hinged arms 506 can include a body 508 having a protrusion 510 at a distal end thereof. The body 508 can be pivoted radially inward to bring the protrusion 510 into the lumen 503 to grasp an instrument or other object inserted therethrough. The locking ring 504 can slide over the hinged arms 506a, 506b to move the arms from the open configuration to the closed configuration and to prevent the arms 506a, 506b from moving relative to the shaft 502, thereby locking the arms in the closed configuration.

Figure 9C:
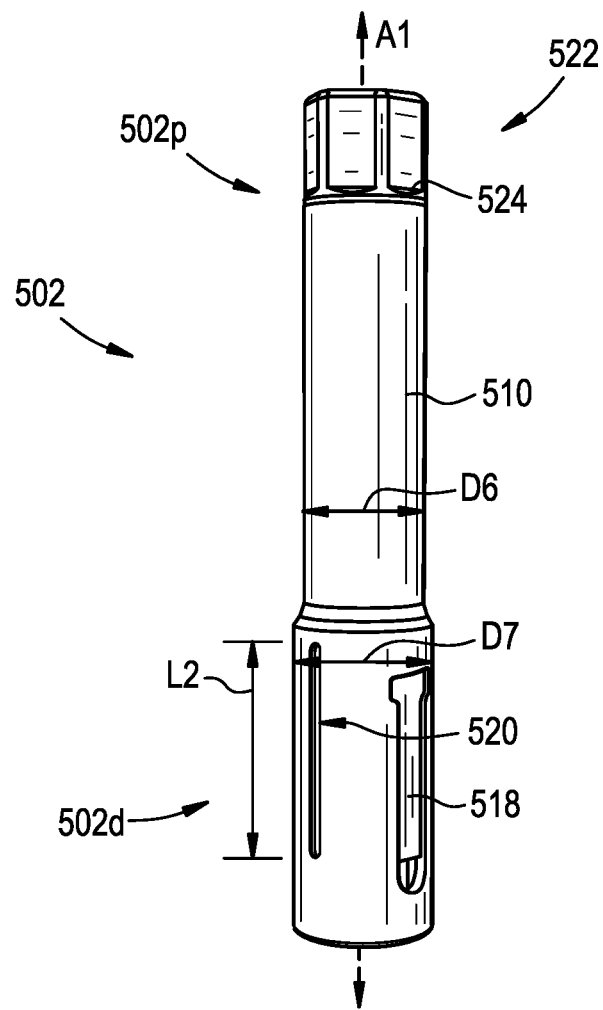
FIG. 9C is a perspective view of a shaft of the derotation assembly of FIG. 9A.
Figure 9D:
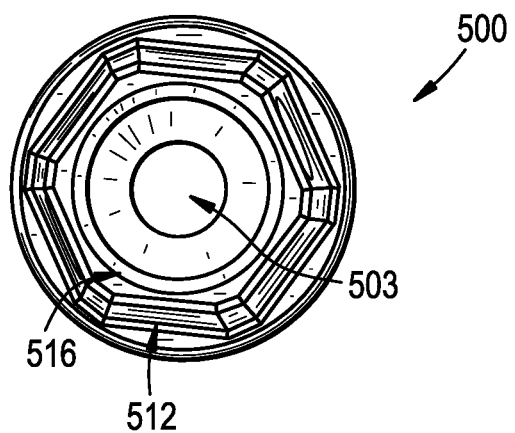
FIG. 9D is an end view of the shaft of FIG. 9C.

FIGS. 9C-9D illustrate the shaft 502 of the derotation assembly 500. The shaft 502 can include a generally cylindrical body defined by an exterior sidewall 510. The shaft 502 can have a cylindrical shape, as shown, or can have various other shapes, such as oval, oblong, square, rectangular, triangular, and so forth. The shape of the lumen 503 can correspond to that of the shaft, as shown, or the lumen 503 can have a different shape than the shaft, such as oval, oblong, square, circular, rectangular, triangular, and so forth. The lumen 503 can extend along the axis A1 from a proximal end 502p to a distal end 502d of the shaft 502. The lumen 503 can receive instruments or tools therethrough for performing rod reduction, derotation, drilling, set screw insertion, and so forth. The instruments can be inserted proximally or distally through the lumen 503.

The shaft 502 can include a distal drive interface 512 configured to mate with the drive interface of the reduction instrument 300. For example, the interior of the lumen 503 can include a hex, hexalobe, pentalobe, or other drive interface 512. The drive interface 512 can be in communication with the lumen 503 such that tools inserted through the drive interface 512 can pass through at least a portion of the lumen 503, and tools inserted through the lumen 503 can pass through at least a portion of the drive interface 512. The drive interface 512 and the lumen 503 can be separated by an abutment surface or shoulder 516 that is defined by the interior sidewall 510 of the shaft, as shown in FIG. 9D. The abutment surface 516 can prevent an instrument inserted into the drive interface 512 from advancing too far proximally into the lumen 503.

The shaft 502 can include a proximal portion 502p and a distal portion 502d. The proximal portion 502p can be integrally formed with the distal portion 502d or can be attached thereto via various mechanisms, such as a threaded, welded, snap-fit, interference, or other connection. In some embodiments, the proximal portion 502p can have a diameter D6 and the distal portion 502d can have a larger diameter D7, or the shaft 502 can have a uniform diameter throughout. As shown the diameter D6 of the proximal portion 502p is smaller than the diameter D7 of the distal portion 502d, though the diameter of the distal and proximal portions can vary relative to one another. In some embodiments, the proximal portion 502p can be made from the same material as the distal portion 502d, or the proximal and distal portions can be made from different materials.

The shaft 502 can include one or more cut-outs therein that define one or more cavities 518 in which parts of the assembly can be disposed. As shown, the shaft 502 can include opposed cavities 518a, 518b in which the hinged arms 506a, 506b can be disposed. It will be appreciated that a shape of the cavities can correspond with a shape of the hinged arms, though, in some embodiments, the cavities 518a, 518b can have a different shape from the hinged arms 506a, 506b to either limit or increase the degree to which the hinged arms 506a, 506b can pivot. The hinged arms 506a, 506b can be secured to the cavities 518a, 518b by a pin, weld, snap-fit, press-fit, or the like. The hinged arms 506 can be integrally-formed cantilevered portions of the shaft 502. The shaft 502, as shown, includes two cavities 518a, 518b, though, in some embodiments, the shaft can include one cavity or three or more cavities.

The shaft 502 can include one or more pin paths 520 therein. As shown, the shaft 502 can include opposed pin paths 520a, 520b configured to allow the pins 505 to travel therethrough. Each pin path 520a, 520b can have a proximal end 520p and a distal end 520d. Each pin path 520 can be configured to receive the pin 505 coupled to the locking ring 504 therein to allow the locking ring 504 to travel relative to the shaft 502 along the pin path 520, as discussed further below. The pin paths 520a, 520b can have a length L2 that extends from the proximal end 520p to the distal end 520d of the pin path 520. The pin paths 520 can be located on the distal portion 502d, on the proximal portion 502p, or can extend along both portions. The shaft 502 can include two pin paths 520a, 520b as shown, or can include one pin path or three or more pin paths.

The shaft 502 can include a proximal drive interface 522. For example, similar to the drive interface 308 discussed above with regards to the reducer shaft 300 of FIGS. 7A-7F, the shaft 502 can include a hex drive 524 configured to be coupled to an adapter 350, 400, or to another instrument. The drive interface 522 can be located at a proximal end of the shaft 502 as shown, or at any other position along the length of the shaft. It will be appreciated that the drive interface 522 of the shaft 502 can be the same, similar to, or different from the drive interface 308 of the reducer shaft 300.

Figure 9E:
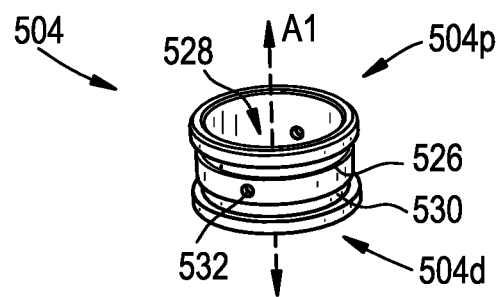
FIG. 9E is a perspective view of a locking ring of the derotation assembly of FIG. 9A.

The locking ring 504 is shown in FIG. 9E. The locking ring 504 can move relative to the shaft 502 to exert a force on the hinged arms 506a, 506b, e.g., to squeeze the arms into engagement with an instrument inserted into the distal drive interface 512 of the shaft 502 and/or to prevent the arms from pivoting radially-outward to disengage from the inserted instrument. The locking ring 504 can include a generally ring-shaped body defined by a sidewall 526 having a central opening 528. The central opening 528 can extend along the axis A1 from a proximal end 504p to a distal end 504d of the locking ring 504.

The locking ring 504 can have a circular shape, as shown, or can have various other shapes, such as oval, oblong, square, rectangular, triangular, and so forth. In some embodiments, the locking ring 504 can correspond with a shape of the shaft 502 on which it is disposed, or with a shape of a shaft through which it travels. The locking ring 504 can be inserted either proximally or distally over the shaft 502.

The locking ring 504 can include one or more holes 532 therein for receiving the pins 505. The holes 532 can align with the pin paths 520a, 520b on the shaft 502 to couple the locking ring 504 thereto. Although two holes 532 are shown, one or three holes can be used in some embodiments to couple the locking ring 504 to the shaft 502. In some embodiments, the number of holes 532 can correspond to the number of pin paths 520 to which the locking ring 504 is coupled.

The locking ring 504 can travel along a portion of the shaft 502 to move the hinged arms 506a, 506b from the open configuration to the closed configuration to secure the shaft 502 to an instrument received within the drive interface 512. The locking ring 504 can have a locked position, in which the locking ring maintains the arms 506 in the closed configuration, and an unlocked position in which the locking ring does not interfere with movement of the arms to the open configuration.

Figure 9F:
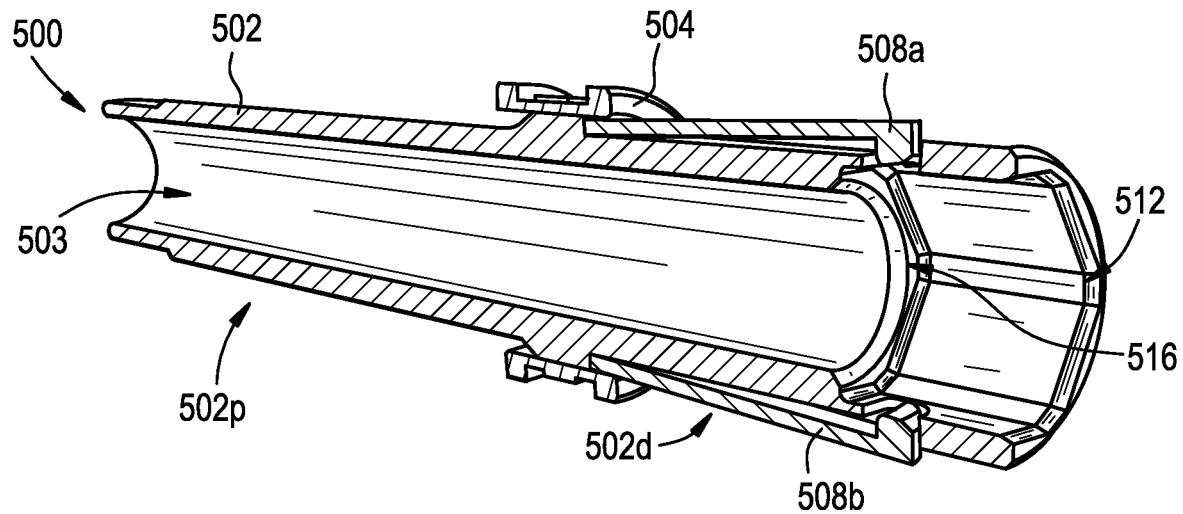
FIG. 9F is a longitudinal sectional perspective view of the derotation assembly of FIG. 9A, shown in an open and unlocked configuration.

FIG. 9F illustrates the derotation assembly 500 with the arms 506 in the open configuration and the locking ring 504 in the unlocked position. In this state, the locking ring 504 can be disposed in a relatively proximal position such that the locking ring 504 exerts little to no inward force on the hinged arms 506. The hinged arms 506 can protrude from an outside surface 502o of the shaft 502. The arms 506 can be disposed outside of the lumen 503 and can be free to move relative to the lumen 503 such that no part of the arms 506 is disposed within the lumen 503, or such that the arms 506 extend into the lumen 503 to a lesser degree. Insertion of an instrument into the shaft 502 while in this state can cause the hinged arms 506 to deflect radially outward from the cavities 518a, 518b and the lumen 503. Once the arms 506 are aligned with a mating feature of the inserted instrument, resilient properties of the arms can cause them to "snap" or move radially inward into engagement with the instrument.

Figure 9G:
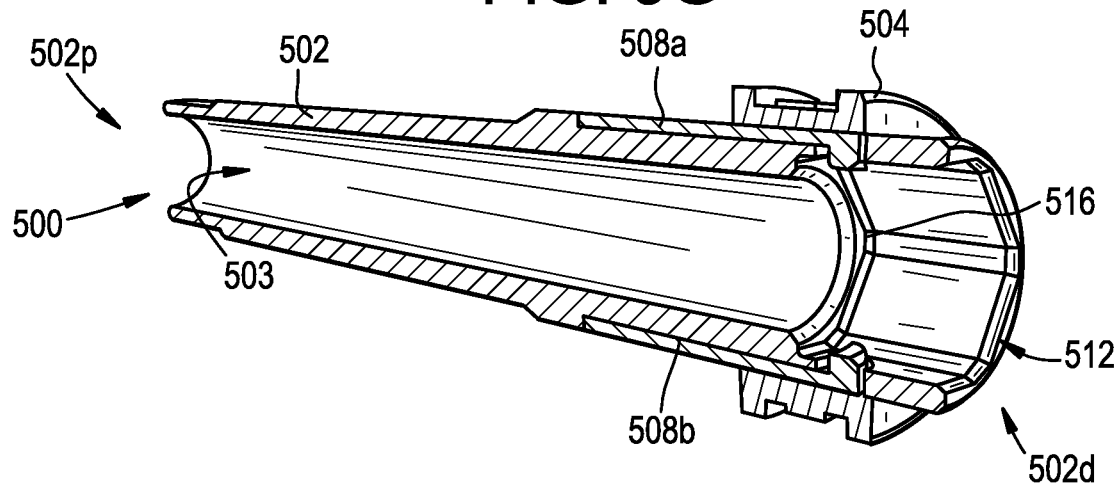
FIG. 9G is a longitudinal sectional perspective view of the derotation assembly of FIG. 9A, shown in a closed and locked configuration.

FIG. 9G illustrates the derotation assembly 500 with the arms 506 in the closed configuration and the locking ring 504 in the locked position. In this state, the locking ring can be disposed in a relatively distal position such that the locking ring 504 exerts an inward force on the hinged arms 506. The force on the hinged arms 506 can move the arms into the closed configuration, and maintain the hinged arms in the closed configuration. In the closed configuration, the hinged arms 506 can be disposed in the cavities 518 so as to align with or be flush with the outside surface 502o of the tube 502. In this position, at least a portion of the arms 506 can be disposed within the lumen 503 to engage and retain an instrument therein, e.g., the drive interface 308 of the reducer shaft 300, to secure the instrument to the assembly 500.

Figure 9H:
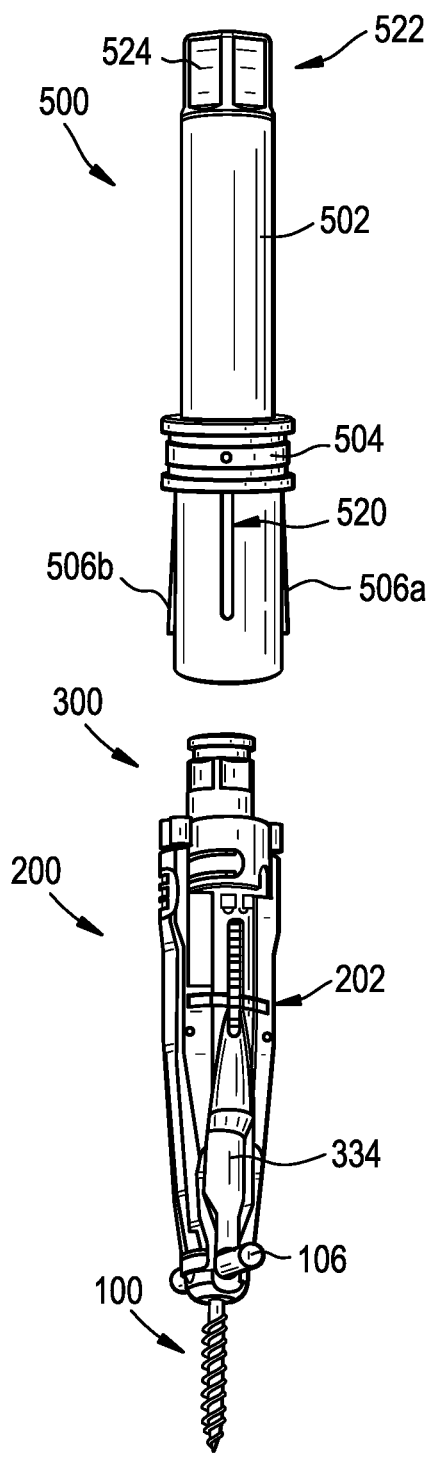
FIG. 9H is a perspective view of the derotation assembly of FIG. 9A, shown in the open and unlocked configuration, being coupled to the reducer shaft of FIG. 7A.
Figure 9I:
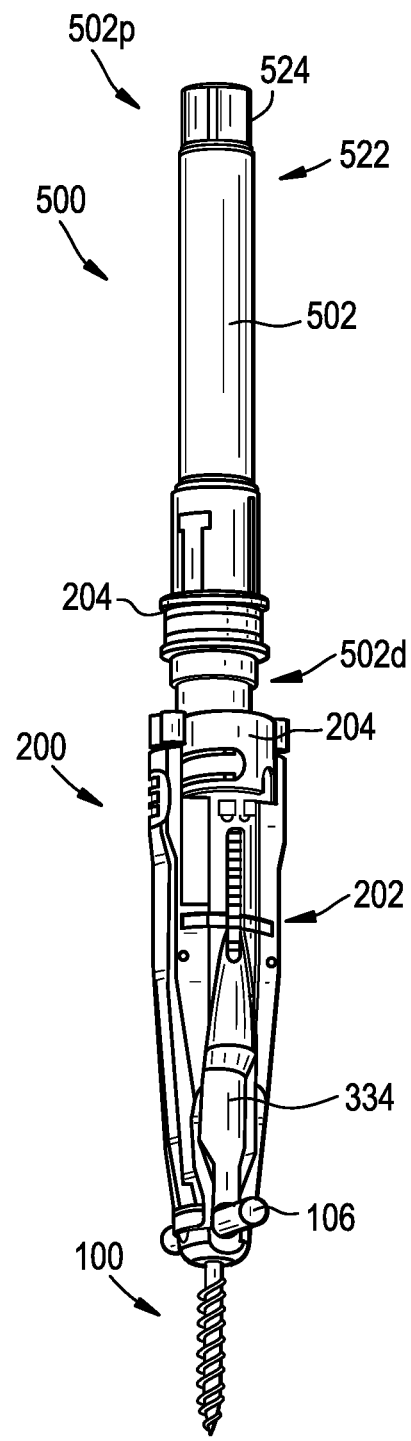
FIG. 9I is a perspective view of the derotation assembly of FIG. 9A, shown in the closed and locked configuration, coupled to the reducer shaft of FIG. 7A.

As shown in FIGS. 9H-9I, the derotation assembly 500 can be coupled to an instrument, e.g., the reducer shaft 300, to apply derotation or other forces to a vertebra or implant to which the instrument body 200 is attached. The derotation assembly 500 can be placed over the drive interface 308 of the reducer shaft 300 with the hinged arms 506 in the open configuration. Once the drive interface 308 is sufficiently disposed in the shaft 502, e.g., such that the shaft 502 abuts the shoulder 314, the locking ring 504 can be advanced distally to move the hinged arms 506 inward to the closed configuration and to lock the arms in the closed configuration.

In the closed configuration, the protrusions 510 of the hinged arms 506a, 506b can be received within the circumferential groove 312 of the reducer shaft 300 to prevent longitudinal translation of the reducer shaft 300 relative to the assembly 500, thereby preventing disengagement of the assembly from the reducer shaft 300. Derotation or other forces can be applied to the assembly 500 and, by extension, to the reducer shaft 300, instrument body 200, and/or bone anchor 100. In some embodiments, an instrument for inserting a set screw or other closure mechanism can be passed through the lumen 503 of the derotation assembly 500 and through the lumen 302 of the reducer shaft 300, with or without a set screw loaded therein, to apply the set screw to the receiver member 104 of the bone anchor assembly 100. It will be appreciated that the derotation assembly 500 can be attached to the reducer shaft 300 prior to the spinal rod 106 being reduced. For example, the derotation assembly 500 can be attached to a reducer shaft 300 that has not yet been inserted through the instrument body 200. In such a case, the reducer shaft 300 can be inserted and advanced through the instrument body 200 to reduce the spinal rod 106 while having the derotation assembly 500 attached thereto. Rotational forces for advancing the reducer shaft 300 can be applied to the derotation assembly 500, which can transfer said forces to the reducer shaft 300.

FIGS. 10A-10H illustrate one method of using the instruments disclosed herein for docking, rod reduction, derotation, and set screw insertion in a spinal surgery. Except as indicated below and will be readily appreciated by one having ordinary skill in the art, the steps of the described method can be performed in various sequences, and one or more steps can be omitted or added. A detailed description of every sequence of steps is omitted here for the sake of brevity.

As shown in FIG. 10A, a bone anchor 100 can be implanted in a body 1 of a patient, e.g., in a pedicle or lateral mass of a vertebra of the patient. The instrument body 200 having the locking member 204 in the unlocked position and the reducer shaft 300 disposed therein can be docked to the bone anchor 100. As discussed above, in some embodiments, the instrument body 200 can be docked to the bone anchor 100 without the reducer shaft 300 disposed therein. As the bone anchor 100 is inserted into the distal end of the instrument body 200, the pivoting arms 206a, 206b can pivot in a radially-outward direction when first contacted by the receiver member 104 of the bone anchor and can then move, or snap, in a radially-inward direction to engage a groove or other mating feature of the receiver member 104 of the bone anchor.

Once the arms 206 of the instrument body 200 are mated to the bone anchor 100, the locking member 204 can be moved into the locked position, as shown in FIG. 10B, for example by rotating or sliding the locking member 204 relative to the central body 210. In the locked position, the orientation of the blocking portion 259 of the locking member 204 between the pivoting arms 206a, 206b and the central body 210 can keep the pivoting arms 206a, 206b engaged with the bone anchor 100 and prevent the arms 206a, 206b from pivoting away from and releasing the bone anchor. A spinal rod 106 can be inserted through the rod slot of the instrument body 200, between the fixed arms 232a, 232b thereof. The spinal rod 106 can be inserted in an orientation that aligns with the rod-engaging arms 334a, 334b of the reducer shaft 300. An adapter 400 can be engaged with the drive interface 308 of the reducer shaft 300.

As shown in FIG. 10C, the adapter 400 can be used to rotate the reducer shaft 300 (or a portion thereof) relative to the instrument body 200, thereby urging the rod 106 distally into the rod seat of the bone anchor 100. As discussed above, the adapter 400 can mate to the reducer shaft 300 without locking thereto to allow the adapter 400 to easily be moved between multiple instruments.

As shown in FIG. 10D, the adapter 400 can be decoupled from the reducer shaft 300 and a set screw 602 can be inserted into the proximal end of the reducer shaft 300 and passed therethrough into engagement with the receiver member 104 of the bone anchor 100. A set screw driver or inserter instrument 604 can be passed through the reducer shaft 300 and can be manipulated to attach the set screw to the bone anchor, for example by rotating the set screw about the axis A1. The set screw 602 can be tightened to the receiver member 104, e.g., to secure the position of the spinal rod 106 within the bone anchor assembly 100 and/or to lock polyaxial movement of the bone anchor assembly.

FIGS. 10E-10F show the derotation assembly 500 being coupled to the drive interface 308 of the reducer shaft 300. The drive interface 308 can be received in the drive interface 512 of the shaft 502 to align the shaft 502 with the reducer shaft 300 coaxially along the axis A1. The derotation assembly 500 can be in the unlocked configuration with the hinged arms 506a, 506b in the open position, or free to move to the open position, when the derotation assembly is mated to the reducer shaft 300. Once the derotation assembly 500 is mated, the locking ring 504 can be moved distally along the length of the shaft 502 to move the derotation assembly 500 into the locked configuration and forcing the hinged arms 506a, 506b into the closed position. In the closed position, the hinged arms 506a, 506b can grasp the drive interface 308 of the reducer shaft 300 to couple the derotation assembly 500 to the reducer shaft 300. After coupling, a force can be imparted onto the derotation assembly 500 to perform a derotation maneuver or other desired manipulation. The derotation assembly 500 can be coupled to a derotation rack of the type known in the art. Pliers or other tools can be used with the derotation assembly 500 to apply compression or distraction forces to the vertebra.

Rod reduction can be performed before, during, and/or after attaching the derotation assembly 500. The derotation assembly 500 can be rotated, e.g., via an adapter 400 or otherwise, to in turn rotate the reduction shaft 300 and urge the spinal rod 106 towards the bone anchor.

Set screw insertion and/or tightening can be performed before, during, and/or after attaching the derotation assembly 500. For example, FIG. 10G illustrates a set screw 602 and a set screw driver or inserter 604 being passed through the lumen 503 of the derotation assembly 500, through the lumen of the reduction shaft 300, and into the bone anchor 100.

To remove the instrument body 200 from the bone anchor assembly 100, the locking member 204 can be moved from the locked position to the unlocked position. Once the locking member 204 is in the unlocked position, the pivoting arms 206a, 206b can be free to pivot radially-outward with respect to the housing 202 to release from the bone anchor. The heads 262a, 262b of the pivoting arms 206a, 206b can be pressed radially-inward towards the axis A1 to move the bodies 264a, 264b and the fingers 274a, 274b radially-outward with respect to the axis A1. Outward movement of the fingers 274 can withdraw the fingers from a groove or other feature of the bone anchor 100, allowing the arms 206a, 206b to disengage from the bone anchor. The instrument body 200, reduction shaft 300, and the derotation assembly 500 can then be removed from the bone anchor 100.

It will be appreciated that the derotation assembly 500 and/or the reducer shaft 300 can be removed from the instrument body 200 prior to the instrument body 200 being disengaged from the bone anchor assembly 100. For example, in some embodiments, after the set screw 602 is inserted, the locking ring 504 can be moved proximally relative to the shaft 502 to unlock the derotation assembly 500. Proximal movement of the locking ring 504 can allow the pivoting arms 506a, 506b to pivot radially-outward from the shaft 502 to disengage from the drive interface 308 of the reducer shaft 300. Once the arms 506a, 506b are disengaged, the derotation assembly 500 can be removed from the reduction shaft 300. The locking member 204 can then be moved into the unlocked position to remove the instrument body 200 from the bone anchor assembly 100, before or after removing the reduction shaft 300 from the instrument body.

In some embodiments, the instrument body 200 can remain connected to the bone anchor 100 throughout any one or more of (i) bone anchor driving, (ii) rod reduction, (iii) derotation, (iv) compression, (v) distraction, (vi) set screw insertion, and (vii) set screw tightening. For example, rod reduction and set screw insertion can be performed on a bone anchor without detaching the instrument body from the bone anchor between said steps. As another example, rod reduction, derotation, and set screw insertion can be performed on a bone anchor without detaching the instrument body from the bone anchor between said steps.

The instruments described herein can reduce the overall size and number of instruments required for a surgery. The instruments described herein can decrease the number of surgical steps involved with reduction and/or derotation. This can include decreasing the number of times an instrument needs to be docked and undocked from the bone anchor and the number of instruments that need to be passed in and out of the surgical site to address surgical steps.

The instruments described herein can allow a reducer shaft to be inserted into the instrument body without having to pre-load a set screw onto the reducer shaft. Rather, the set screw can be inserted later through a working channel in the reducer shaft.

The instruments described herein can allow an instrument body to be docket to a bone anchor without relying on an inserted reducer shaft to maintain the connection between the instrument body and the bone anchor. The instrument body can be configured such that it only contacts the bone anchor along a lateral sidewall of a receiver member of the bone anchor and not along a proximal-facing end surface of the receiver member.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The instruments and methods disclosed herein can be used in minimally-invasive surgery and/or open surgery. While the instruments and methods disclosed herein are generally described in the context of spinal surgery on a human patient, it will be appreciated that the methods and instruments disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A surgical instrument, comprising:
an instrument body that extends from a proximal end to a distal end to define a working channel therebetween, the distal end terminating in a pair of opposed fixed arms having a recess formed therein that is in communication with the working channel; a pair of pivoting arms received in the recesses of the opposed fixed arms such that a portion of the pair of pivoting arms extends through the recess into the working channel to engage a bone anchor assembly disposed between the pair of opposed fixed arms, a portion of a length of the pair of pivoting arms intersecting a plane that is located at a midpoint of the instrument body and oriented transverse to a longitudinal axis of the working channel;
wherein the pair of pivoting arms are movable:
relative to the instrument body such that the pair of pivoting arms splay outwards when passing over a first portion of the bone anchor assembly and move towards one another to engage a second portion of the bone anchor assembly; and
between a locked position and an unlocked position, wherein:
in the locked position, the pair of pivoting arms are engaged with the bone anchor assembly and are prevented from moving relative to the instrument body; and
in the unlocked position, the pair of pivoting arms are free to move relative to the instrument body.

2. The instrument of claim 1, further comprising a reducer shaft that extends from a proximal portion to a distal portion and defines a lumen therebetween.

3. The instrument of claim 2, wherein an outer diameter of the reducer shaft is smaller than the inner diameter of the working channel to allow the reducer shaft to pass therethrough.

4. The instrument of claim 2, wherein at least a portion of the reducer shaft is configured to rotate relative to the instrument body about a central longitudinal axis thereof to advance the reducer shaft distally relative to the instrument body.

5. The instrument of claim 2, wherein the proximal portion is configured to rotate relative to the instrument body to advance the reducer shaft distally relative to the instrument body.

6. The instrument of claim 2, wherein the distal portion is configured to be rotationally-fixed relative to the instrument body, the distal portion comprising a distal-facing rod-engaging surface that aligns with a rod slot defined between the fixed arms of the instrument body.

7. The instrument of claim 6, wherein the distal-facing rod-engaging surface is rotationally offset from the pivoting arms of the instrument body such that the distal-facing rod-engaging surface advances distally when the reducer shaft is advanced through the instrument body without interfering with the engagement between the pivoting arms and a bone anchor assembly disposed therebetween.

8. The instrument of claim 2, wherein the lumen is configured to receive one or more instruments therethrough.

9. The instrument of claim 2, wherein the proximal portion further comprises an interface to facilitate coupling to an instrument.

10. The instrument of claim 9, wherein the proximal portion further comprises an exterior thread configured to mate with an interior threaded surface of the instrument body to rotate the proximal portion to advance the reducer shaft distally.

11. The instrument of claim 2, wherein the proximal portion further comprises an exterior thread configured to mate with an interior threaded surface of the instrument body.

12. The instrument of claim 2, further comprising a locking member rotatably or slidably disposed on the instrument body.

13. The instrument of claim 12, wherein the locking member is configured to be actuated relative to the instrument body to prevent the pivoting arms from pivoting or to advance the reducer shaft distally through the instrument body.

14. The instrument of claim 12, wherein movement of the locking member is configured to move the pair of pivoting arms between the unlocked position and the locked position.

15. The instrument of claim 12, wherein the locking member is unitary.

16. A surgical instrument, comprising:
an instrument body that extends from a proximal end to a distal end to define a working channel therebetween, the distal end terminating in a pair of opposed fixed arms having a recess formed therein that is in communication with the working channel;
a reducer shaft that extends from a proximal portion to a distal portion and defines a lumen therebetween, the proximal portion including an exterior thread configured to mate with an interior threaded surface of the instrument body; and
a pair of pivoting arms received in the recesses of the opposed fixed arms such that a portion of the pair of pivoting arms extends through the recess into the working channel to engage a bone anchor assembly disposed between the pair of opposed fixed arms;
wherein the pair of pivoting arms are movable:
relative to the instrument body such that the pair of pivoting arms splay outwards when passing over a first portion of the bone anchor assembly and move towards one another to engage a second portion of the bone anchor assembly; and
between a locked position and an unlocked position, wherein:
in the locked position, the pair of pivoting arms are engaged with the bone anchor assembly and are prevented from moving relative to the instrument body; and
in the unlocked position, the pair of pivoting arms are free to move relative to the instrument body.

17. The instrument of claim 16, wherein the proximal portion is configured to rotate relative to the instrument body to advance the reducer shaft distally relative to the instrument body.

18. The instrument of claim 16, wherein the distal portion is configured to be rotationally-fixed relative to the instrument body, the distal portion comprising a distal-facing rod-engaging surface that aligns with a rod slot defined between the fixed arms of the instrument body.

19. The instrument of claim 18, wherein the distal-facing rod-engaging surface is rotationally offset from the pivoting arms of the instrument body such that the distal-facing rod-engaging surface advances distally when the reducer shaft is advanced through the instrument body without interfering with the engagement between the pivoting arms and a bone anchor assembly disposed therebetween.

20. The instrument of claim 16, wherein the proximal portion further comprises an interface to facilitate coupling to an instrument.

* * * * *